United States Patent
Li et al.

(10) Patent No.: US 10,365,385 B2
(45) Date of Patent: *Jul. 30, 2019

(54) APPARATUS, METHOD AND SYSTEM FOR SPARSE DETECTOR

(71) Applicant: SHANGHAI UNITED IMAGING HEALTHCARE CO., LTD., Shanghai (CN)

(72) Inventors: Hongdi Li, Houston, TX (US); Shaohui An, Shanghai (CN); Yun Dong, Shanghai (CN); Yang Lv, Shanghai (CN); Lingzhi Hu, Shanghai (CN); Jun Bao, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/024,070

(22) Filed: Jun. 29, 2018

(65) Prior Publication Data

US 2018/0321400 A1 Nov. 8, 2018

Related U.S. Application Data

(63) Continuation of application No. 15/029,228, filed as application No. PCT/CN2015/100069 on Dec. 31, 2015.

(51) Int. Cl.
- *G06K 9/00* (2006.01)
- *G01T 1/29* (2006.01)
- (Continued)

(52) U.S. Cl.
CPC ............ *G01T 1/2928* (2013.01); *A61B 6/032* (2013.01); *G01N 23/046* (2013.01);
(Continued)

(58) Field of Classification Search
CPC .... A61B 6/032; G01N 23/046; G01T 1/2018; G01T 1/1603; G01T 1/2006
(Continued)

(56) References Cited

U.S. PATENT DOCUMENTS

| 5,777,331 A | 7/1998 | Muehllehner |
| 6,956,214 B2 | 10/2005 | Wong et al. |

(Continued)

FOREIGN PATENT DOCUMENTS

| CN | 103064102 A | 4/2013 |
| CN | 103158203 A | 6/2013 |

(Continued)

OTHER PUBLICATIONS

Yusheng, Li et al., LOR-Interleaving Image Reconstruction for PET imaging with fractional-crystal collimation, Phys. Med. Bio., 60: 647-670 (2015).

(Continued)

*Primary Examiner* — Charlotte M Baker
(74) *Attorney, Agent, or Firm* — Metis IP LLC

(57) ABSTRACT

An apparatus, system, and method involving one or more sparse detectors are provided. A sparse detector may include an array of scintillator crystals generating scintillation in response to radiation and an array of photodetectors generating an electrical signal in response to the scintillation. A portion of the scintillator crystals may be spaced apart by substituents or gaps. The distribution of the substitutes or gaps may be according to a sparsity rule. At least a portion of the array of photodetectors may be coupled to the array of scintillator crystals. An imaging system including an apparatus that may include one or more sparse detectors is provided. The imaging system may include a processor to process the imaging data acquired by the apparatus or system including the one or more sparse detectors. The
(Continued)

method may include preprocess the acquired image data and produce images by image reconstruction.

20 Claims, 13 Drawing Sheets

(51) Int. Cl.
| | | |
|---|---|---|
| *G01T 1/16* | (2006.01) | |
| *G01T 1/20* | (2006.01) | |
| *G01T 1/202* | (2006.01) | |
| *A61B 6/03* | (2006.01) | |
| *G01N 23/046* | (2018.01) | |

(52) U.S. Cl.
CPC ............ *G01T 1/1603* (2013.01); *G01T 1/202* (2013.01); *G01T 1/2006* (2013.01); *G01T 1/2018* (2013.01); *G01T 1/2985* (2013.01)

(58) Field of Classification Search
USPC .......................................................... 382/131
See application file for complete search history.

(56) References Cited

U.S. PATENT DOCUMENTS

| | | | |
|---|---|---|---|
| 8,229,199 B2 | 7/2012 | Chen et al. | |
| 8,472,688 B2 | 6/2013 | Samsonov et al. | |
| 8,849,002 B2 | 9/2014 | Chinn et al. | |
| 2003/0095631 A1* | 5/2003 | Rosner .................. | G01N 23/02 378/98.12 |
| 2007/0098138 A1 | 5/2007 | Bessho | |
| 2011/0127436 A1 | 6/2011 | Hashizume et al. | |
| 2013/0320222 A1 | 12/2013 | Abenaim et al. | |
| 2014/0138548 A1 | 5/2014 | Li et al. | |
| 2014/0264041 A1 | 9/2014 | Schulz et al. | |
| 2015/0221085 A1 | 8/2015 | Ueki et al. | |
| 2016/0183893 A1 | 6/2016 | Zhang et al. | |

FOREIGN PATENT DOCUMENTS

| | | | |
|---|---|---|---|
| CN | 103376459 A | 10/2013 | |
| CN | 103592671 A | 2/2014 | |
| CN | 103668465 A | 3/2014 | |
| CN | 104077763 A | 10/2014 | |
| CN | 104166151 A | 11/2014 | |
| CN | 105425270 A | 3/2016 | |
| WO | 2015019312 A1 | 2/2015 | |
| WO | WO 2015019312 A1 * | 2/2015 | ........... A61B 6/0407 |

OTHER PUBLICATIONS

Sidky E Y et al., Accurate image reconstruction from few-views and limited-angle data in divergent-beam CT, Journal of X-ray Science and Technology, 14(2): 119-139 (2006).
Valiollahzadeh S et al., Image recovery in PET scanners with partial detector rings using compressive sensing, 2012 IEEE Nuclear Science Symposium and Medical Imaging Conference Record, 3036-3039 (2012).
Chinn G et al., Sparse Signal Recovery Methods for Multiplexing PET Detector Readout, IEEE Transactions on Medical Imaging, 32(5): 932-942 (2013).
Malczewski K, PET image Reconstruction using compressed sensing, Signal Processing: Algorithms, Architectures, Arrangements, and Applicants, 176-181 (2013).
Salomon A et al. Sparse crystal setting and large axial FOV for intergrated whole-body PET/MR, 2011 IEEE Nuclear Science Symposium Conference Record, 2521-2523 (2011).
Zhang Y et al., CT Image Reconstruction Algorithm Based on Anisotropic Total Variation Minimization, Computer Science and Application,4: 240-247 (2014).

* cited by examiner

APPARATUS, METHOD AND SYSTEM FOR SPARSE DETECTOR

CROSS-REFERENCE TO RELATED APPLICATIONS

The present application is a continuation application of U.S. patent application Ser. No. 15/029,228, filed on Apr. 13, 2016, which is a U.S. national stage application under 35 U.S.C. § 371 of International Application No. PCT/CN2015/100069, filed on Dec. 31, 2015, designating the United States of America, the contents of which are hereby incorporated by reference.

TECHNICAL FIELD

This application relates to an imaging technology, and more particularly, to a sparse detector and an imaging method and system using a sparse detector.

BACKGROUND

A scintillator is a material that may exhibit scintillation. A scintillator may absorb ionizing radiation and emit a fraction of the absorbed energy as light. For example, an incoming particle, such as a gamma photon, incident on the scintillator may create an energized electron, either by Compton scattering or by photoelectric absorption; as the energized electron passes through the scintillator, it may lose energy and excite one or more other electrons; the excited electron(s) may decay to the ground state, giving off light. As such, the scintillator may produce photons of visible or ultraviolet light corresponding to incoming particles that interact with the scintillator material. The intensity of the light pulses may be proportional to the energy deposited in the scintillator by the incoming particles.

A detector may be formed by coupling a scintillator to an electronic light sensor, i.e. a photodetector. Detectors are widely used in radiation detection in many fields including, for example, Homeland Security radiation detection, neutron and high energy particle physics experiments, new energy resource exploration, X-ray detection, nuclear cameras, gas exploration, etc. Merely by way of example, detectors are also widely used in medical imaging technology such as Computed Tomography (CT) and Positron Emission Tomography (PET).

Scintillators used in, for example, the medical imaging technology, may be manufactured with materials containing rare earth elements such as, for example, Lanthanum, Lutetium, Yttrium, etc. Scintillators containing rare earth elements may be expensive due to factors including, for example, the difficulty of crystallization, the scarcity of economically exploitable ore deposits, etc. The costs for an apparatus, system and/or method involving one or more scintillators may be high. Therefore, it is desired to lower the costs of such an apparatus, system and/or method lower costs.

SUMMARY

In a first aspect of the present disclosure, an apparatus is provided. The apparatus may include a sparse detector. The sparse detector may include an array of scintillator crystals generating scintillation in response to radiation. At least a portion of the scintillator crystals may be spaced apart according to a sparsity rule. The sparse detectors may further include an array of photodetector elements configured to generate an electrical signal in response to the scintillation. At least a portion of the array of photodetector elements may be coupled to the array of scintillator crystals.

In some embodiments, at least a portion of the array of scintillator crystals may be spaced apart by one or more blocks of a light-transmitting material. In some embodiments, the size of at least some of the one or more blocks of the light-transmitting material may be substantially equal to the size of a scintillator crystal of the array of scintillator crystals. In some embodiments, the light-transmitting material may include glass.

In some embodiments, the apparatus may include a gap between two scintillator crystals of the array of scintillator crystals. In some embodiments, the size of the gap may be substantially equal to the size of one scintillator crystal of the array of scintillator crystals.

In some embodiments, at least a portion of scintillator crystals are spaced based on a sparsity rule. In some embodiments, the sparsity rule may designate a way of substituting scintillator crystals in a non-sparse detector with substituents according to a sparsity rule to obtain a sparse detector. For illustration purposes, a sparsity rule may be described by comparing a sparse detector to a non-sparse detector. Compared to a non-sparse detector, a sparse detector according to a sparsity rule may be formed by substituting at most one scintillator crystal out of every two neighboring scintillator crystals, with a substituent, among the array of scintillator crystals. The description does not suggest that to form a sparse detector, a non-sparse detector is formed, and some scintillator crystals are removed from the non-sparse detector to make room for substituents or gaps.

In alternative embodiments, the sparsity rule may specify a sparseness. In some embodiments, a sparsity rule that may be applied to the sparse detector may specify a sparseness of 1% to 50%, or 10% to 40%, or 20% to 30%.

In some embodiments, the shape of the sparse detector may be a block, an arc, a ring, a rectangle, or a polygon. In some embodiments, the apparatus may include one, two, or more sparse detectors. In some embodiments, the apparatus may include two sparse detector modules parallel to each other, a detector module including a plurality of sparse detectors. In some embodiments, the apparatus may include detector modules forming a polygon, a detector module including a plurality of sparse detectors. In some embodiments, the apparatus may include sparse detectors forming a ring.

In a second aspect of the present disclosure, an imaging system is provided. The imaging system may include an apparatus including one or more sparse detectors that may generate imaging data. A sparse detector may include an array of scintillator crystals generating scintillation in response to radiation. At least a portion of the scintillator crystals may be spaced apart. The sparse detectors may further include an array of photodetector elements configured to generate an electrical signal in response to the scintillation. At least a portion of the array of photodetector elements may be coupled to the array of scintillator crystals. The imaging system may further include a processor configured to generate, based on the imaging data, an image.

In some embodiments, the imaging system may be a single modality imaging system. The single modality imaging system may include a CT system, a PET system, a Digital Radiography (DR) system, a Single Photon Emission Computed Tomography (SPECT) system, an X-ray scan, and an ultrasound scan. In some embodiments, the imaging system may be a multi-modality imaging system. The multi-modality imaging system may include a Computed Tomography-Positron Emission Tomography (CT-PET) system, a Computed Tomography-Magnetic Resonance Imaging (CT-MRI) system, a Positron Emission Tomography-Magnetic Resonance Imaging (PET-MRI) system, a Single Photon Emission Computed Tomography-Positron Emission Tomography (SPECT-PET) system.

In a third aspect of the present disclosure, a method is provided. The method may include providing an apparatus including a sparse detector, acquiring imaging data using the apparatus, preprocessing the imaging data and obtaining preprocessed imaging data, and reconstructing an image based on the preprocessed imaging data. The sparse detector may include an array of scintillator crystals generating scintillation in response to radiation. At least a portion of the scintillator crystals may be spaced apart. The sparse detectors may further include an array of photodetector elements configured to generate an electrical signal in response to the scintillation. At least a portion of the array of photodetector elements may be coupled to the array of scintillator crystals.

In some embodiments, the preprocessing step may further include generating virtual scintillator units according to the sparsity rule of the sparse detector, calculating the efficiency of the virtual scintillator units, and calculating the efficiency of the line of response (LOR).

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 5A illustrates an apparatus including two detector modules according to some embodiments of the present disclosure, FIG. 5B illustrates a apparatus including four detector modules according to some embodiments of the present disclosure, FIG. 5C illustrates an apparatus including eight detector modules according to some embodiments of the present disclosure, and FIG. 5D illustrates an apparatus including a plurality of detectors forming a ring according to some embodiments of the present disclosure;

FIG. 6A illustrates a non-sparse detector according to some embodiments of the present disclosure, and FIG. 6B illustrates a sparse detector according to some embodiments of the present disclosure;

FIG. 7A illustrates the indirect coupling between the scintillator and photodetector according to some embodiments of the present disclosure, and FIG. 7B illustrates the direct coupling between the scintillator and photodetector according to some embodiments of the present disclosure;

FIG. 8A illustrates the one to one coupling between the scintillator and the photodetector in a lateral view according to some embodiments of the present disclosure, FIG. 8B illustrates the one to one coupling between a scintillator crystal and a photodetector according to some embodiments of the present disclosure, and FIG. 8C illustrates the one to one coupling between a substituent and a photodetector according to some embodiments of the present disclosure;

DETAILED DESCRIPTION

Figure 1:
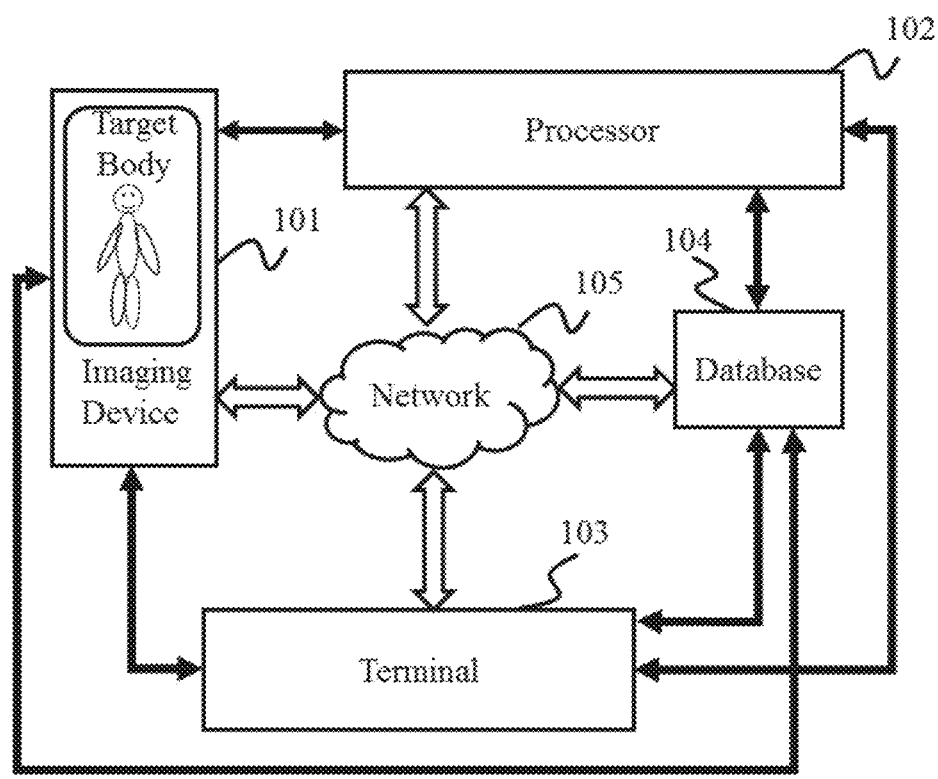
FIG. 1 is an illustration of an imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

This disclosure relates to an imaging technology, and more particularly, to a sparse detector imaging method and system. The system may include a sparse detector including an array of scintillator crystals. In some embodiments, at least a portion of the scintillator crystals may be spaced apart according to a sparsity rule to form a sparse detector array. The configuration of the sparse detector array may be such that the amount of scintillator material used to build the detectors in the system may be reduced and that the system may be used to generate images of desirable quality.

FIG. 1 is an illustration of an imaging system according to some embodiments of the present disclosure. In some embodiments, the imaging system may be a single modality imaging system. The single modality imaging system may include, for example, a Computed Tomography (CT) system, a Positron Emission Tomography (PET) system, a Digital Radiography (DR) system, a Single Photon Emission Computed Tomography (SPECT) system, etc. In some embodiments, the imaging system may be a multi-modality imaging system. The multi-modality imaging system may include, for example, a Computed Tomography-Positron Emission Tomography (CT-PET) system, a Computed Tomography-Magnetic Resonance Imaging (CT-MRI) system, a Positron Emission Tomography-Magnetic Resonance Imaging (PET-Mill) system, a Single Photon Emission Computed Tomography-Computed Tomography (SPECT-CT) system. The operating mechanisms of different imaging modalities may be the same or different according to some embodiments of the present disclosure. Accordingly, the imaging data acquired by different imaging modalities may also be the same or different. Particularly, in some embodiments, the imaging data of different modalities may complement one another, thereby providing a set of imaging data describing a target from different analytical angles. For example, in some embodiments, the multi-modality imaging may achieve the merging of morphological and functional images. The exemplary imaging systems described herein that may be used in connection with the present system are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

As illustrated in FIG. 1, the imaging system may include an imaging device 101, a processor 102, a terminal 103, a database 104, and a network 105. The imaging device 101 may be configured to examine a target. In some embodiments, the imaging device 101 may include a plurality of imaging detectors. An imaging detector may include a scintillator and a photodetector. A plurality of imaging detectors may form a sparse detector array.

The target that may be examined by the imaging device 101 may be any organic or inorganic mass, natural or man-made, that has a chemical, biochemical, biological, physiological, biophysical and/or physical activity or function. Merely by way of example, a target pertaining to the present disclosure may include a cell, a tissue, an organ, a part of or a whole body of a human or an animal. In some embodiments, the target may include a substance, a tissue, an organ, an object, a specimen, a body, or the like, or any combination thereof. In some embodiments, the subject may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof. Other exemplary embodiments may include but not limited to man-made composition of organic and/or inorganic matters that are with or without life. The exemplary targets described herein that may be examined in connection with the present system are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

Figure 5A:
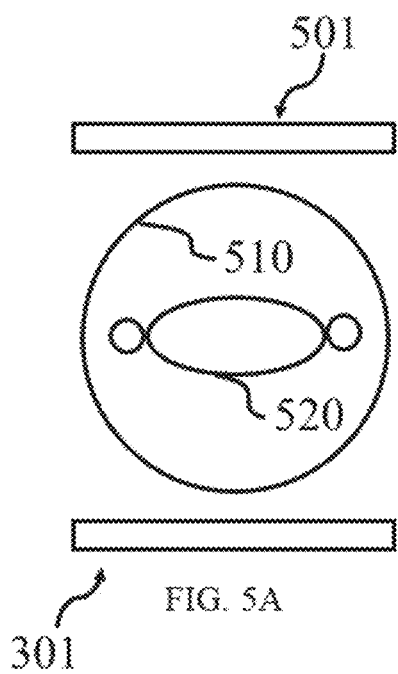
FIGS. 5A through 5D illustrate various configurations of an apparatus according to some embodiments of the present disclosure; specifically.
Figure 5B:
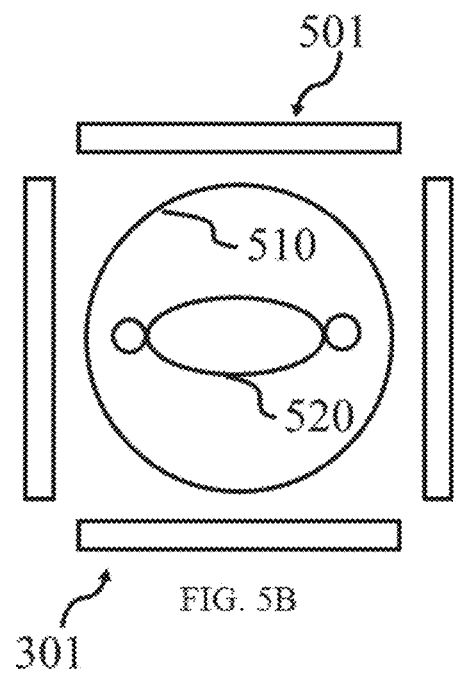
Figure 5C:
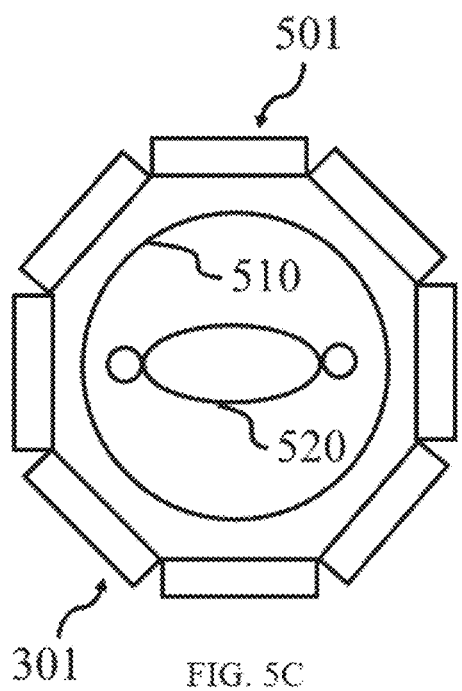

In some embodiments, the imaging device 101 may include a gantry 510 (as shown in FIGS. 5A through 5C). The target 520 may be placed within the gantry 510 during imaging. In some embodiments, the imaging device 101 may not include a gantry. Instead, the target may be placed in front of the imaging device 101. In some embodiments where the target may be a human patient, the human patient may take any suitable position during imaging. Merely by way of examples, the human patient may lie on the back, lie in prone, sit, and stand within the gantry or in front of the imaging device 101.

The processor 102 may be configured to process imaging data. The processor 102 may be configured to perform functions of image processing and imaging device 101 controlling. In some embodiments, the processor 102 may be configured to perform operations including, for example, data preprocessing, image reconstruction, image correction, or the like, or a combination thereof. In some embodiments, the processor 102 may be configured to generate a control signal relating to the configuration of the imaging device 101. In some embodiments, the processor 102 may include any processor-based and/or microprocessor-based units. Merely by way of examples, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof. In some embodiments, the processor 102 may also include a memory. In some embodiments, the memory may include Random Access Memory (RAM). In some embodiments, the memory may include Read Only Memory (ROM). The processor that may be used in connection with the present system described herein are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

The terminal 103 may be configured to receive input and/or display output. The terminal 103 may be configured to communicate with the processor 102 and allow one or more operators to control the production and/or display of images. The terminal 103 may include, for example, a display, a mobile device (e.g., a smart phone, a tablet, a laptop computer, or the like), a personal computer, other devices, or the like, or a combination thereof. Other devices may include a device that may work independently, or a processing unit or processing module assembled in another device (e.g., an intelligent home terminal). The terminal 103 may be configured to receive input. The terminal 103 may include an input device, a control panel (not shown in the figure), etc. The input device may be a keyboard, a touch screen, a mouse, a remote controller, or the like, or any combination thereof. An input device may include alphanumeric and other keys that may be inputted via a keyboard, a touch screen (for example, with haptics or tactile feedback), a speech input, an eye tracking input, a brain monitoring system, or any other comparable input mechanism. The input information received through the input device may be communicated to the processor 102 via, for example, a bus, for further processing. Another type of the input device may include a cursor control device, such as a mouse, a trackball, or cursor direction keys to communicate direction information and command selections to, for example, the processor 102 and to control cursor movement on the display device. The terminal 103 may be configured to display output. Exemplary information may include, for example, an image, a request for input or parameter relating to image acquisition and/or processing, or the like, or a combination thereof. The display device may include a liquid crystal display (LCD), a light emitting diode (LED)-based display, a flat panel display or curved screen (or television), a cathode ray tube (CRT), or the like, or a combination thereof.

The database 104 may be configured to store data. The data to be stored may be from the imaging device 101, the processor 102, the terminal 103, the database 104, and/or the network 105. Exemplary data that may be stored may include imaging data acquired by the imaging device 101, a sparsity rule, a lookup table, the efficiency of a virtual scintillator unit, the efficiency of the line of response, a reconstructed image, etc. In some embodiments, the database 104 may be a hard disk drive. In some embodiments, the database 104 may be a solid-state drive. In some embodiments, the database 104 may be a removable storage drive. Merely by way of examples, a non-exclusive list of removable storage drive that may be used in connection with the present disclosure includes a flash memory disk drive, an optical disk drive, or the like, or a combination thereof.

In some embodiments, the imaging device 101, the processor 102, the terminal 103, and the database 104 may be connected to or communicate with each other directly. In some embodiments, the imaging device 101, the processor 102, the terminal 103, the database 104 may be connected to or communicate with each other via the network 105. The network 105 may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. The network that may be used in connection with the present system described herein are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

It should be noted that the imaging system described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

Figure 2:
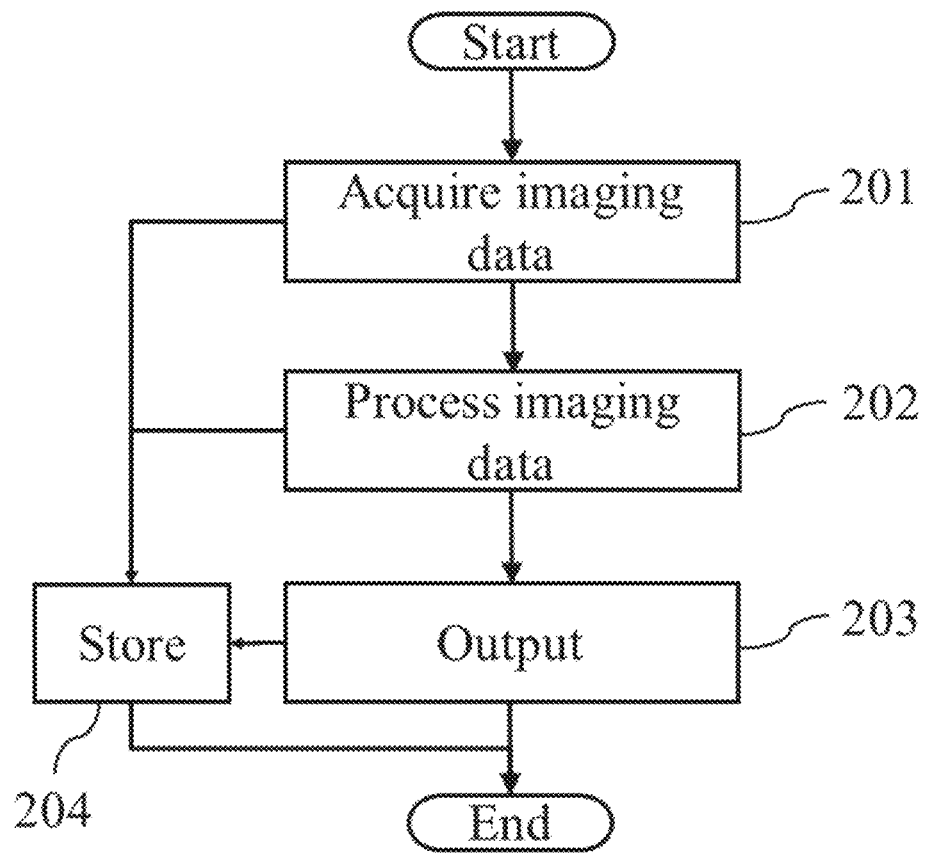
FIG. 2 is a flowchart illustrating a process for an imaging method according to some embodiments of the present disclosure.

FIG. 2 is a flowchart illustrating a process for an imaging method according to some embodiments of the present disclosure. Prior to acquiring imaging data of a target or a portion of a target, the imaging device 101 and/or target may be adjusted to obtain the most advantageous analysis position or angle. The positioning of imaging device 101 and/or the target may be accomplished manually and/or automatically.

As illustrated in step 201, the imaging data of a target may be acquired. The acquisition may be accomplished by the imaging device 101. The imaging device 101 may detect the radiation released from the target and convert the radiation signal into electrical signal. The electrical signal may be further converted to computer-readable signal.

In step 202, the acquired imaging data may be processed. The data processing may include image reconstruction, image correction, and data estimation. The data processing may be executed by the processor 102. In some embodiments, data processing may be performed in parallel to, or, as needed, after all imaging data have been acquired.

In step 203, the system may output the processed imaging data. The output step may be performed by the terminal 103. Merely by way of examples, the processed imaging data may be delivered to a display, printer, computer network, or other device. The output imaging data may also comprise two-dimensional (2D) images, a three-dimensional (3D) volume, or a 3D volume over time (4D).

In step 204, the data generated during step 201, step 202, and step 203 may be stored. Exemplary data that may be stored may include imaging data acquired by the imaging device 101, a pattern of the sparse detectors, a sparsity rule, a lookup table, the efficiency of a virtual scintillator unit, the efficiency of the line of response, reconstructed image, etc. The data may be stored in the database 104. In some embodiments, the method to store may include sequential storage, link storage, hash storage, index storage, or the like, or any combination thereof.

It should be noted that the flowchart described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

Figure 3:
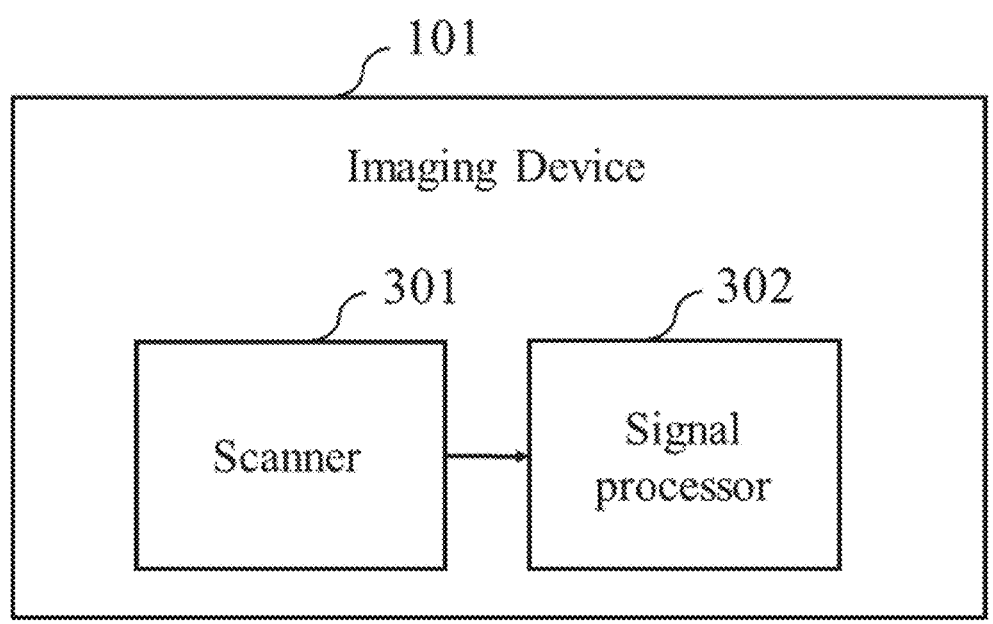
FIG. 3 is a block diagram illustrating the configuration of an imaging device according to some embodiments of the present disclosure.

FIG. 3 is a block diagram illustrating the configuration of an imaging device according to some embodiments of the present disclosure. An imaging device 101 may include an apparatus 301 and a signal processor 302. It should be noted that the imaging device 101 may include other modules or units such as a gantry, a patient table, a high-voltage tank. In some embodiments, the imaging device 101 may further include a radiation generating unit which may be configured to emit radiation in some system, e.g., a CT system, a DR system, a CT-PET system. The radiation generating unit may be a cold cathode ion tube, a high vacuum hot cathode tube, a rotating anode tube, etc.

The apparatus 301 may refer to a device for detecting radiation and provide an output according to the detected radiation. The radiation used herein may include a particle ray, a photon ray, or the like, or a combination thereof. The particle ray may include neutron, proton, electron, μ-meson, heavy ion, or the like, or any combination thereof. The photon ray may include X-ray, γ-ray, α-ray, β-ray, ultraviolet, laser, or the like, or any combination thereof. In some embodiments, the radiation received by the apparatus 301 may come directly from the radiation generating unit or other radiation source. In some embodiments, the radiation received by the apparatus 301 may be the radiation emitted from the target under examination or the radiation traversing the target under examination. For example, in a CT system, the detector may detect the radiation from an X-ray tube and traversing the target under examination. Another example in a PET system, the gamma-ray emitted from the target under examination may be received by the apparatus 301.

In some embodiments of the present disclosure, the apparatus 301 may include one or more detectors. In some embodiments, the apparatus 301 may be a one-dimensional apparatus, a two-dimensional apparatus, a three-dimensional apparatus, etc. The apparatus 301 may assume different configurations. Details regarding the configuration of the apparatus 301 will be further explained in FIGS. 5A through 5C. The numbers of the column and row of detectors in one apparatus may be varied according to the different demands, e.g., image resolution, the whole size of the detector and pixel, cost, or the like. In some embodiments, the detectors may be arranged in a uniform pattern or a non-uniform pattern. For example, the detectors may be arranged to form an angle, which may be arbitrary.

The detector in the apparatus 301 may include a scintillator and a photodetector. The scintillator may include an array of scintillator crystals. The photodetector may include an array of photodetector elements. The scintillator crystals and the photodetector elements may be coupled directly and indirectly. As used herein, coupling may indicate that the optical signal produced in a scintillator crystal or a scintillator may be transmitted to a photodetector or a photodetector element. Details regarding the coupling between the scintillator crystals and the photodetector elements will be further explained in FIGS. 6 through 7. The scintillator crystals in the detector 310 may be arranged tightly or sparsely. The sparsity may be between 1% and 50%, or between 2% and 45%, or between 3% and 40%, or between 4% and 35%, or between 5% and 30%, or below 60%, or below 50%, or below 40%, or below 30%, or below 20%. Merely by way of example, the sparsity may be approximately 10%, or 15%, or 20%, or 25%, or 30%, or 35%, or 40%. The sparsity of each detector may be the same or different. Details regarding the sparseness of the detector will be further explained in FIG. 8.

The scintillator crystal may include any material that has the ability to absorb ionizing radiation and to emit a fraction of the absorbed energy as light. Provided below is a non-exhaustive list of exemplary embodiments of suitable scintillator materials: CdWO4, $BaF_2$, CsF, CsI(Na), CsI(Tl), NaI(Tl), $CaF_2$(Eu), lutetium oxyorthosilicate (LSO) crystals; bismuth germinate (BGO) crystals, gadolinium oxyorthosilicate (GSO) crystals, LYSO crystals, and mixed lutetium silicates (MLS) crystals. The size of the scintillator crystal may vary according to one or more conditions including, for example, image resolution, sensitivity, stability, the size of the detector or the like, or any combination thereof. The size of the scintillator crystals in the detector may be the same or various. Merely by way of example, the length and/or width of the scintillator may range from several micrometers to several hundred micrometers. For instance, the height of the scintillator may range from several micrometers to several hundred micrometers, e.g., 500 micrometers. The shape of the cross-section of a scintillator crystal may be circular, oval, rectangular, or the like, or any combination thereof. As used herein, the long axis of a scintillator crystal is the direction perpendicular to the base to which the scintillator crystal is attached when it is packaged into a detector. A cross-section of a scintillator crystal is a plane within the scintillator crystal that is perpendicular to the long axis thereof.

The photodetector element may be a photoelectric conversion element. A photoelectric conversion element may firstly detect an optical signal and then may convert the optical signal into an electrical signal including, e.g., electrical current, electrical voltage, and/or other electrical phenomena. The photodetector element in some embodiments of the present disclosure may include a phototube, a Photomultiplier Tube (PMT), a photodiode, an active-pixel sensor, a bolometer, a CCD, a gaseous ionization detector, a photoresistor, a phototransistor, Avalanche Photodiode (APD), Single-Photon Avalanche Photodiode (SPAD), Silicon Photomultiplier (SiPM), Digital Silicon Photomultiplier (DSiPM), or the like, or any combination thereof. The size of the photodetector element may vary based on one or more conditions including, for example, image resolution, sensitivity, stability, the size of the scintillator, the size of the scintillator crystal, or the like, or any combination thereof. Merely by way of example, the length and/or width of the photodetector element may range from several micrometers to several hundred micrometers. Merely by way of example, the height of the photodetector may range from several micrometers to several hundred micrometers, e.g., 500 micrometers. The cross-section of a photodetector element may be circular, oval, rectangular, or the like, or any combination thereof. The photodetector element may be arranged regularly, or irregularly. As used herein, the long axis of a photodetector element is the direction perpendicular to the base to which the photodetector element is attached when it is packaged into a detector. A cross-section of a photodetector element is a plane within the photodetector element that is perpendicular to the long axis thereof.

It should be noted that the above description about the detector is merely an example according to the present disclosure. Obviously, to those skilled in the art, after understanding the basic principles of the detector, the form and details of the detector may be modified or varied without departing from the principles. The modifications and variations are still within the scope of the current disclosure described above. For example, the number of detector in the apparatus may be one, two, three, or any number based on the actual demand. In some embodiments, the radiation generating unit may include several X-ray tubes.

The signal processor 302 of the imaging device 101 may be configured to convert the radiation received by the apparatus 301 to imaging data. The term "imaging data" used herein may refer to the data based on signals detected by the detectors and used to reconstruct an image. The signal processor 302 may generate some imaging data based on the output from the photodetector elements. In some embodiments, the signal processor 302 may measure the time that radiation may be received by the apparatus 301, calculate the radiation energy received by the apparatus 301, and determine the position of the radiation traversing the target under examination, or the like, or any combination thereof.

For example, in a PET system, when a PET tracer molecule is introduced into the target, positrons may be emitted by the PET tracer molecule. After moving a distance, e.g., 1 micrometer, the positrons may undergo annihilations with the electrons and electron-positron annihilations may result in two 511 keV gamma photons, which upon their own generation, begin to travel in opposite directions with respect to one another. This process may be referred as a coincidence event. A coincidence event is assigned to a line of response (LOR) joining the two relevant detectors. Because of the different trajectories of the two gamma photons, the time that the gamma photons are detected by the detectors may be different. The signal processor 302 may measure the difference of the time a pair of gamma photons received by the two relevant detectors respectively, determine the position of annihilation, calculate the radiation energy received by the two relevant detector, and calculate the number of coincidence events. The signal processor 302 may perform the process mentioned above based on the signals from the photodetector.

It should be noted that the above description about the signal processor is merely an example according to the present disclosure. Obviously, to those skilled in the art, after understanding the basic principles of the signal processor, the form and details of the signal processor may be modified or varied without departing from the principles. The modifications and variations are still within the scope of the current disclosure described above. For example, the signal processor may amplify, digitize, and/or analyze the signal from the photodetector before measuring the detection time, calculating the position, calculating the energy and/or counting the number.

Figure 4:
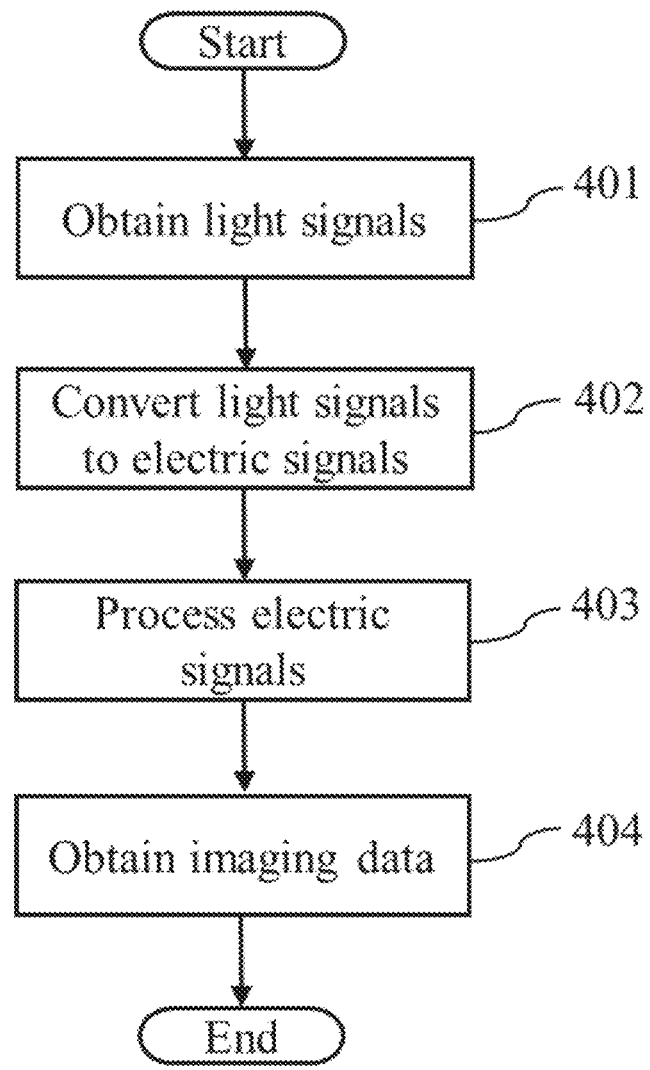
FIG. 4 is a flowchart illustrating a process for obtaining imaging data with an imaging device according to some embodiments of the present disclosure.

FIG. 4 is a flowchart illustrating a process for obtaining imaging data of an imaging device according to some embodiments of the present disclosure. It should be noted that process described below is merely provided for illustrating an example of the radiation imaging, and not intended to limit the scope of the present disclosure. The radiation used herein may include a particle ray, a photon ray, or the like, or a combination thereof. The particle ray may include neutron, proton, electron, μ-meson, heavy ion, or the like, or any combination thereof. The photon beam may include X-ray, γ-ray, α-ray, β-ray, ultraviolet, laser, or the like, or any combination thereof.

As illustrated in FIG. 4, in step 401, light signals are obtained. This process may be performed by the scintillator or other components that may sense radiation and convert it to light. Before this step, the radiation may be generated. In some embodiments, the radiation may come from a radiation generating unit such as an X-ray tube. In some embodiments, the radiation may be generated by electron-positron annihilation. The positrons may be emitted by tracer molecules introduced into a target. After the radiation is generated, the radiation may be converted into the form of visible or invisible light.

The light signals may then be converted into electrical signals in step 402. This step may be performed by the photodetectors in the apparatus 301. The photodetectors may sense the light signals emitted from the scintillator and convert them into corresponding electrical signals. Exemplary embodiments of a photodetector element that may be used in connection with the present system include Photomultiplier Tube (PMT), Avalanche Photodiode (APD), Single-Photon Avalanche Photodiode (SPAD), Silicon Photomultiplier (SiPM), Digital Silicon Photomultiplier (DSiPM). The exemplary photodetectors described herein that may be used in connection with the present system described above are not exhaustive and are not limiting; numerous other changes, substitutions, variations, alterations, and modifications may be ascertained to one skilled in the art and it is intended that the present disclosure encompass all such changes, substitutions, variations, alterations, and modifications as falling within the scope of the present disclosure.

The obtained electrical signals may be processed in step 403. This step may be performed by the signal processor 302 or other modules or units in the system. In some embodiments, based on the electrical signals, the signal processor 302 may record the time radiation was detected, assess the radiation energy, assess the amount of the radiation received by the apparatus 301, determine the position of the radiation traversing the target under examination, or the like, or any combination thereof. In some embodiments, the signal processor 302 may calculate the number of coincidence events. Besides, the signal processor 302 may amplify, digitize, and/or analyze the signal from a photodetector.

After the electrical signals are processed, imaging data may be obtained in step 404. The imaging data may be used to reconstruct an image of the target under examination. Image reconstruction may be performed by other components of the imaging system, or by an image processing device or system outside of the imaging system.

It should be noted that the above description about the process of obtaining imaging data is merely an example according to the present disclosure. Obviously, to those skilled in the art, after understanding the basic principles of the process of obtaining imaging data, the form and details of the process may be modified or varied without departing from the principles. In some embodiments, other steps may added in the process. For example, the intermediated data and/or the final data of the process may be stored in the process. The modifications and variations are still within the scope of the current disclosure described above.

FIGS. 5A through 5C illustrate different configurations that the apparatus 301 may assume according to some embodiments of the present disclosure. FIGS. 5A through 5C illustrate a position relationship of the apparatus 301, a gantry 510, and a target 520. The apparatus may include a plurality of detector modules 501 as shown in the figures. In some embodiments, the apparatus may include two or more plurality of detector modules 501. A detector module 501 may include one or more detectors. The gantry 510 may have a circular cross-section as shown in FIGS. 5A through 5C. In some embodiments, the gantry 510 may have a cross-section of any other shapes suitable for imaging. Merely by way of examples, the gantry 510 may have a rectangular cross-section, an elliptical cross-section, a polygonal cross-section, etc. The gantry 510 may have cross-sections of various shape and/or size along the direction perpendicular to the cross-sections. A target 520 to be examined may be placed in the gantry 510. In some embodiments, the detector modules 501 may be positioned circumferentially around the gantry 510. In some embodiments, the detector modules 501 may not be positioned around the gantry 510 but right next to the target 520. In some embodiments, the detector modules 501 may be fixed on a patient table (not shown in the figure). In some embodiments, the detector modules 501 may be stationary during imaging. In some embodiments, the detector modules 501 may be circumferentially movable around the target 520. In some embodiments, one of the detector modules 501 may be independently movable with respect to another detector module 501.

As shown in FIG. 5A, the apparatus 301 may include two detector modules 501. The side of scintillators of one detector module may face or oppose the side of scintillators of the other detector module. In some embodiments, the two detector modules 501 may be parallel to each other. In some embodiments, the two detector modules 501 may be at an angle (for example, an oblique angle or a right angle) with to each other. In some embodiments, the two detector modules 501 may be positioned symmetrically about the center of the gantry 510. In some embodiments, the two detector modules 501 may be positioned asymmetrically about the center of the gantry 501.

FIG. 5B illustrates another configuration of the apparatus 301 according to some embodiments of the present disclosure. As shown in FIG. 5B, the apparatus 301 may include four detector modules 501. In some embodiments, the angle between neighboring detector modules 501 may be approximately 90 degrees. The four detector modules 501 may surround a gantry 510. A target 520 may be placed within the gantry. In some embodiments, the four detector modules may not surround a gantry 510 but be positioned right next to the target 520. The sides of scintillators of the detector modules 501 may face the target 520. Two detection detector modules 501 may form a pair. The sides of the scintillators of the pair of detector modules 501 may face each other.

FIG. 5C illustrates another configuration of the apparatus 301 according to some embodiments of the present disclosure. As shown in FIG. 5C, the apparatus 301 may include eight detector modules 501. In some embodiments, the eight detector modules 501 may substantially form an octagon. The eight detector modules 501 may distribute evenly with each detector module 501 facing a separate octant of a 360-degree field. The sides of scintillators of the detector modules 501 may face the target 520. Two detection detector modules 501 may form a pair. The sides of the scintillators of the pair of detector modules 501 may face each other.

Figure 5D:
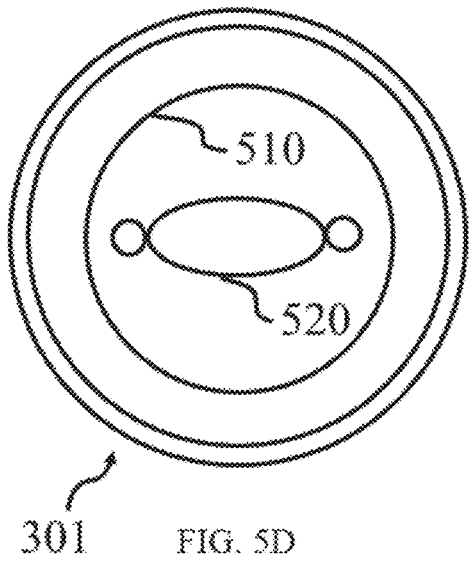

FIG. 5D illustrates another configuration of the apparatus 301 according to some embodiments of the present disclosure. As shown in FIG. 5D, the apparatus 301 may include a plurality of detectors forming a ring. The ring formed by the plurality of detector modules may be concentric with respect to the gantry 510. The sides of scintillators of the detector modules in the ring may face the target 520. The sides of scintillators of the detector modules opposing each other may face each other.

It should be noted that the configurations of detectors described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

In some embodiments, a detector module 501 may include a sparse detector. A sparse detector may refer to a detector having at least a portion of scintillator crystals spaced apart based on a sparsity rule.

Figure 6A:
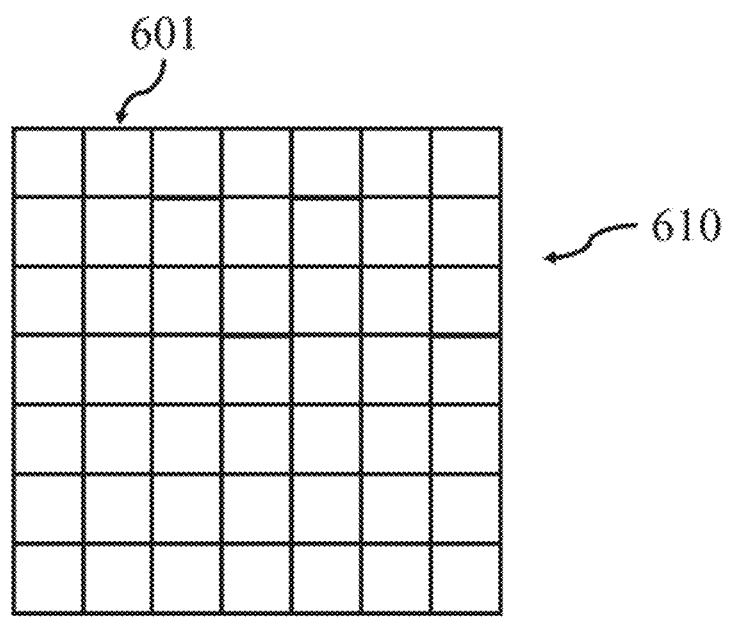
FIGS. 6A through 6B illustrates the configurations of scintillators in a detector according to some embodiments of the present disclosure; specifically.
Figure 6B:
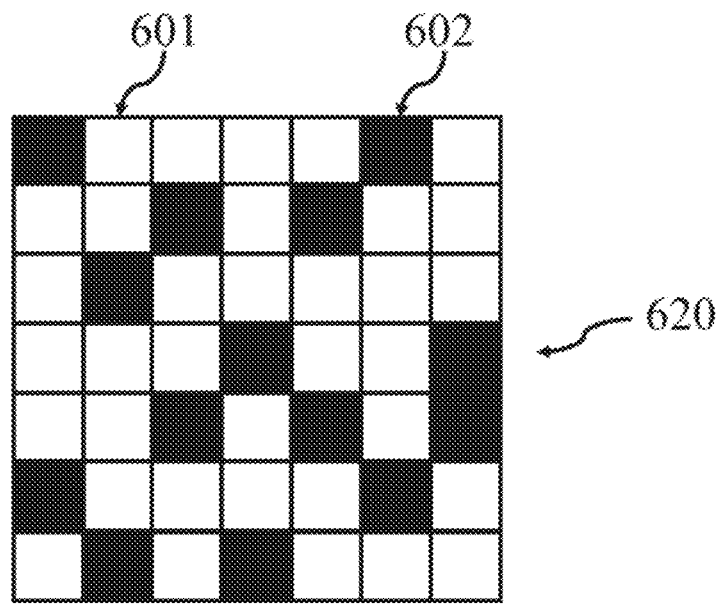

FIGS. 6A and 6B illustrate a non-sparse detector and a sparse detector according to some embodiments of the present disclosure, respectively. As shown in FIG. 6A, the scintillator 610 in a non-sparse detector may include an array of scintillator crystals 601 packed together and not spaced apart.

FIG. 6B illustrates a scintillator 620 of a sparse detector. As shown in FIG. 6B, the scintillator 620 may include scintillator crystals 601 and substituents or gaps 602. In some embodiments, at least a portion of the scintillator crystals 601 may be spaced apart by the substituents or gaps 602. In some embodiments, at least a portion of the scintillator crystals 601 may be spaced apart by the substituents 602. In some embodiments, at least a portion of the scintillator crystals 601 may be spaced apart by gaps 602. In some embodiments, the sparse detector may include both substituents and gaps, and at least a portion of the scintillator crystals 601 may be spaced apart by either the substituents or the gaps 602.

The substituent 602 may be a light-transmitting material. The substituent 602 may be in the solid state, the liquid state, or the gas state. Merely by way of examples, the substituent 602 may be glass, air, or one or more other materials. In some embodiments, one substituent 602 may occupy the same volume as one scintillator crystal. The ratio of the volume of said substituents to the volume of a scintillator may be up to 60%, or up to 50%, or up to 40%, or up to 30%, or up to 25%, or up to 20%, or up to 15%, or up to 10%, or up to 8%, or up to 5%. In some embodiments of the present disclosure, the space between the sidewalls of neighboring scintillator crystals in a scintillator 620 may be filled with a reflective material to increase the internal reflection along the sidewalls of the crystals, while decreasing the crosstalk between the neighboring crystals. As used herein, a sidewall of a scintillator crystal may refer to a wall forming the side of the scintillator crystal that may be parallel or substantially parallel to the long axis of the scintillator crystal.

The sparsity of the sparse detector 620 may follow a sparsity rule. In some embodiments, the sparsity rule may designate a way of creating a sparse detector by substituting one or more scintillator crystals in a non-sparse detector with substituents or gaps.

Merely by way of examples, a sparsity rule for a sparse detector, as opposed to a non-sparse detector, may be to group scintillator crystals of a non-sparse detector into subsets containing a first number of scintillator crystals, and in one or more subsets, to substitute one or more scintillator crystals with one or more substituents or gaps. The subsets of scintillator crystals may include an equal, or a various first numbers of scintillator crystals. For example, a subset of scintillator crystals may include two, three, four, five, or any number of scintillator crystals. The scintillator crystals in a subset may be neighboring, partially neighboring, or completely surrounded by substituents or gaps. In some embodiments, every scintillator crystal of the subset is next to at least one scintillator crystal of the subset. In some embodiments, at least two of the scintillator crystals in a subset are next to each other; at least two of the scintillator crystals in a subset are spaced apart by a substituent or gap. In some embodiments, a subset of scintillator crystals containing at least partially neighboring scintillator crystals may exhibit a geometric pattern. For example, in some embodiments, a subset of scintillator crystals may include four at least partially neighboring scintillator crystals positioned in one direction (for example, along a line, etc.), scintillator crystals positioned in two directions (for example, exhibiting an L-shape, a square, a T-shape, a rectangle, etc.).

The subsets of scintillator crystals may be spaced according to a same sparsity rule or a different sparsity rule. The sparsity rule may include the number of substituent(s) in a subset (i.e. the second number), the position(s) of the substituent(s) relative to the position(s) of the scintillator crystal(s) in the subset, the number of scintillator crystal(s) in the subset (i.e. the first number), or the like, or a combination thereof. For example, the second number of scintillator crystals in a subset may be zero, one, two, three, or any number smaller than, or equal to the first number of scintillator crystals in the subset. In some embodiments, the sparseness of a subset, i.e., the ratio of the second number of substituents or gaps in a subset to the first number of scintillator crystals in a subset, may be between 1% to 50%, or between 2% and 45%, or between 3% and 40%, or between 4% and 35%, or between 5% and 30%, or below 60%, or below 50%, or below 40%, or below 30%, or below 20%. The sparseness of each subset may be equal or various. In some embodiments, the overall sparseness of the sparse detector may be between 1% to 50%, or between 2% and 45%, or between 3% and 40%, or between 4% and 35%, or between 5% and 30%, or below 60%, or below 50%, or below 40%, or below 30%, or below 20%.

Merely by way of examples, possible sparsity rules that may be used in connection with some embodiments of the present disclosure may include: to substitute at most one scintillator crystal out of a subset of two neighboring scintillator crystals with a substituent or a gap, to substitute no more than one scintillator crystal out of a subset of three neighboring scintillator crystals with a substituent or a gap, to substitute no more than two scintillator crystals out of a subset of five neighboring scintillator crystals with a substituent or a gap, or the like, or any combination thereof. For example, a sparsity rule may include two types of subsets of scintillator crystals containing two and three scintillator crystals in each subset, respectively, and at most one scintillator crystal out of a subset of two neighboring scintillator crystals with a substituent or a gap, no more than one scintillator crystal out of a subset of three neighboring scintillator crystals with a substituent or a gap. It is understood that the description is for illustrating exemplary structures, configurations, or scintillator crystal layout of a sparse detector as opposed to a non-sparse detector, and is not intended to illustrate or suggest a way of manufacturing a sparse detector. For instance, the description of "to substitute at most one scintillator crystal out of two neighboring scintillator crystals with a substituent or a gap" does not suggest that to form a sparse detector, a non-sparse detector is formed, and some scintillator crystals are removed from the non-sparse detector to make room for substituents or gaps.

In some embodiments, the sparse detector may exhibit a periodic pattern of scintillator crystals being spaced apart. As used herein, the term "periodic pattern" may refer to that a periodic unit including the geometric pattern exhibited by each subset of scintillator crystals and the substituents or gaps between the scintillator crystals repeats in a sparse detector. A periodic unit may include one or more subsets.

Merely by way of example, in some embodiments, a sparse detector may follow a sparsity rule to substitute one scintillator crystals in a subset of two neighboring scintillator crystals, and the one substituted scintillator crystals may occupy the same relative position of the two neighboring scintillator crystals (for example, imagine that a column of scintillator crystals along the circumferential direction of a gantry is taken and spread out as a rectangle in front of us, and we are looking from left to right, the left one or the right one of the two neighboring scintillator crystals in a subset is always substituted). In this example, the periodic unit may include a subset of two neighboring scintillator crystals and the one substituted scintillator crystals positioned as described above. A sparse detector exhibiting such a pattern may be referred to as exhibiting a periodic pattern.

As another example, in some embodiments, a sparse detector following more than sparsity rules may exhibit a periodic pattern as well. For example, in some embodiments, a sparse detector may follow a sparsity rule to substitute at most one scintillator crystals in a subset of two neighboring scintillator crystals. A subset in such occasions may exhibit three geometric patterns, e.g., pattern one of non-substitution, pattern two of the left one of the subset of two scintillator crystals being substituted, and pattern three of the right one of the subset of two scintillator crystals being substituted. The three pattern may all exist in a sparse detector. In some embodiments, the three patterns may form a periodicity following a certain order. In further detail, the first subset may exhibit pattern one, the second subset may exhibit pattern two to the right of the first subset, the third subset may exhibit pattern three to the right of the second subset, the fourth subset may exhibit pattern one again, the fifth subset may exhibit pattern two to the right of the fourth subset, the sixth subset may exhibit pattern three to the right of the fifth subset, and so forth. In this example, a periodic unit may include three subsets, the first subset exhibiting pattern one, the second subset may exhibiting pattern two positioned to the right of the first subset, and the third subset exhibiting pattern three positioned to the right of the second subset.

A sparse detector may include a plurality of periodic units. A periodic unit may include at least 10 scintillator crystals, or at least 20 scintillator crystals, or at least 30 scintillator crystals, or at least 40 scintillator crystals, or at least 50 scintillator crystals, or at least 60 scintillator crystals, or at least 70 scintillator crystals, or at least 80 scintillator crystals, or at least 90 scintillator crystals, or at least 100 scintillator crystals. A periodic unit may include at least 10 substituents or gaps, or at least 20 substituents or gaps, or at least 30 substituents or gaps, or at least 40 substituents or gaps, or at least 50 substituents or gaps, or at least 60 substituents or gaps, or at least 70 substituents or gaps, or at least 80 substituents or gaps, or at least 90 substituents or gaps, or at least 100 substituents or gaps. In a periodic unit, the scintillator crystals are spaced apart by the substituents or gaps according to one or more sparsity rules.

It is understood that the periodic order described above is merely an example and is not intended to limit, the subsets exhibiting patterns may follow any possible orders applicable. In some embodiments, the first group of subsets may exhibit pattern one, the second group of subsets may exhibit pattern two, the third group of subsets may exhibit pattern three, the fourth group of subsets may exhibit pattern one again, and so forth. A group of subsets may include any number of subsets of scintillator crystals, such as five, ten, twenty, fifty, and a hundred.

In some embodiments, the sparse detector may exhibit a random pattern of scintillator crystals being spaced apart. By "random pattern" used herein it may refer to that the subsets of the scintillator crystals exhibit no periodic geometric pattern or no period units. Using the examples described in the previous paragraph that a sparse detector follows a sparsity rule that to substitute at most one scintillator crystals of a subset of two neighboring scintillator crystals. In such a subset, none or one scintillator crystals may be substituted by substituents or gaps. The substituted scintillator crystals may be any one of the two neighboring scintillator crystals. In such occasion, a subset of two neighboring scintillator crystals may exhibit three possible geometric pattern. The three patterns may not be periodic. The overall the sparse detector may exhibit a random pattern of scintillator crystals being spaced apart.

The sparse detector that may be used in connection with the present system described herein are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

Figure 7A:
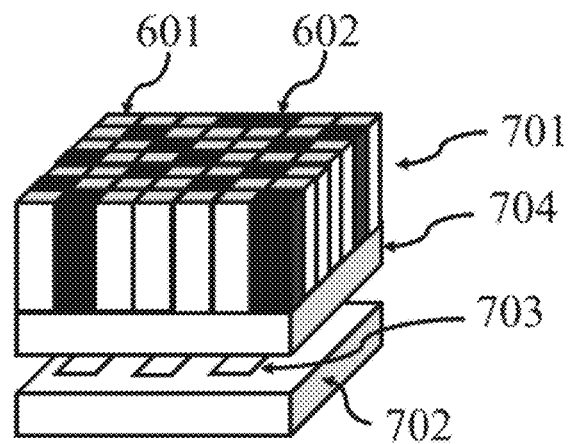
FIGS. 7A through 7B illustrate the direct and indirect coupling between the scintillator and the photodetector according to some embodiments of the present disclosure; specifically.

FIG. 7A illustrates the indirect coupling between the scintillator and the photodetector via the light guide according to some embodiments of the present disclosure. The scintillator and photodetector as illustrated may form a sparse detector. In some embodiments, the scintillator 701 may include an array of scintillator crystals 601 and substituents or gaps 602 between the scintillator crystals of the array. The scintillator crystals 601 may be spaced apart by the substituents or gaps 602. The distribution of the substituents or gaps 602 may be according to a sparsity rule.

The photodetector 702 may include an array of photodetector elements 703. In some embodiments, the number of the photodetector elements 703 on the photodetector 702 may be equal to the number of scintillator crystals 601 and substituents or gaps 602 on the scintillator 701. In such embodiments, the scintillator crystals 601 and substituents or gaps 602 may be coupled to the photodetector elements 703 in a one-to-one pattern. In some embodiments, the number of photodetector elements 703 on the photodetector 702 may be unequal to the number of scintillator crystals 601 and substituents or gaps 602 on the scintillator 701. In such embodiments, multiple scintillator crystals 601 and/or substituents or gaps 602 may be coupled to a photodetector element 703. Merely by way of examples, four of the scintillator crystals 601 and substituents or gaps 602 may be coupled to one photodetector element 703. In some embodiments, the number of photodetector elements 703 on the photodetector 702 may be equal to the number of scintillator crystals 601 on the scintillator 701. In such embodiments, one scintillator crystal 601 may be coupled to one photodetector element 703, and a substituent or gap 602 may be not coupled to a photodetector element 703.

A light guide 704 may be used to transmit the light coming out from the scintillator 701 to the photodetector 702. The light guide 704 may spread the light signals (or referred to as optical signals) outputted by a single scintillator crystal within the array of scintillator crystals such that it may be detected by at least one photodetector element. In some embodiments, the light guide 704 may include a light transmitting intermediate, e.g., an optical fiber, an optical fiber bundle, an optical glue, an optically coupling material, an immersion oil, or the like, or a combination thereof. In some embodiments, the scintillator 701 may be optically coupled to the photodetector 702 via one or more optical fibers or optical fiber bundles. One end of the optical fiber may be attached to the output end of the scintillator 701, and the other end of the optical fiber may be attached to the input end of the photodetector 702. In various embodiments, an optical fiber bundle may assume various configurations with respect to, for example, length, width, etc.

Figure 7B:
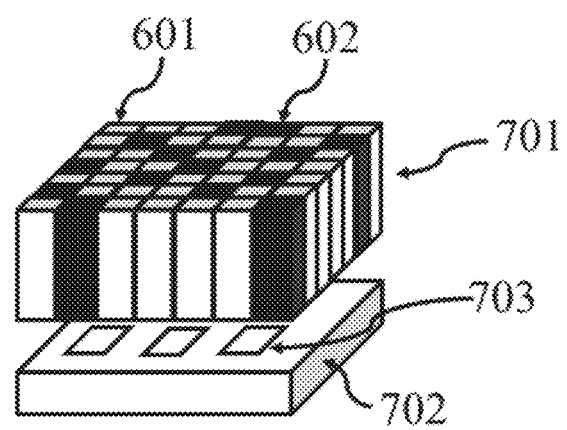

FIG. 7B illustrates the direct coupling between the scintillator 701 and the photodetector 702 according to some embodiments of the present disclosure. The scintillator 701 and the photodetector 702 as illustrated may form a sparse detector. In some embodiments, the scintillator 701 may include an array of scintillator crystals 601 and substituents or gaps 602 between the scintillator crystals 601 of the array. The scintillator crystals 601 may be spaced apart by the substituents or gaps 602. The distribution of the substituents or gaps 602 may be according to a sparsity rule.

The photodetector 702 may include an array of photodetector elements 703. In some embodiments, the number of the photodetector elements 703 on the photodetector 702 may be equal to the number of scintillator crystals 601 and substituents or gaps 602 on the scintillator 701. In such embodiments, the scintillator crystals 601 and substituents or gaps 602 may be coupled to the photodetector element 703 in a one-to-one pattern. In some embodiments, the number of photodetector elements 703 on the photodetector 702 may be unequal to the number of scintillator crystals 601 and substituents or gaps 602 on the scintillator 701. In such embodiments, multiple scintillator crystals 601 and/or substituents or gaps 602 may be coupled to a photodetector element 703. Merely by way of examples, four of the scintillator crystals 601 and substituents or gaps 602 may be coupled to one photodetector element 703. In some embodiments, the number of photodetector elements 703 on the photodetector 702 may be unequal to the number of scintillator crystals 601 and substituents or gaps 602 on the scintillator 601. In such embodiments, a portion of scintillator crystal 601 may be coupled to one photodetector element 703, and a portion of substituent or gap 602 may be not coupled to photodetector element 703. Merely by way of examples, one scintillator crystal 601 may be coupled to one photodetector element 703, while the substituents or gaps 602 may be uncoupled to photodetector elements 703.

A light guide may be unnecessary. As shown in FIG. 7B, the scintillator 701 may be directly coupled to the photodetector 702 without the use of a light guide. Particularly, the output end of the scintillator 701 may be directly coupled to the input end of the photodetector 702.

It should be noted that the coupling between the scintillator and the photodetector described above is provided for the purposes of illustration, and not intended to limit the scope of the present disclosure. Apparently for persons having ordinary skills in the art, numerous variations and modifications may be conducted under the teaching of the present disclosure. However, those variations and modifications may not depart the protecting scope of the present disclosure.

Figure 8A:
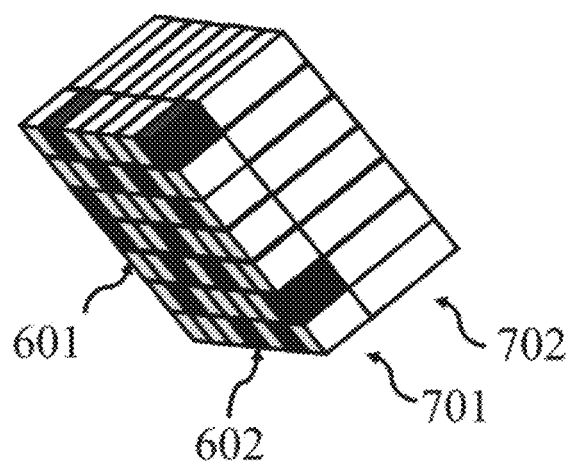
FIGS. 8A through 8C illustrate the one to one coupling between the scintillator and the photodetector according to some embodiments of the present disclosure; specifically.

FIG. 8A illustrates the one-to-one coupling between the scintillator and the photodetector according to some embodiments of the present disclosure. The scintillator and the photodetector as illustrated may form a sparse detector. In some embodiments, the scintillator 701 may include an array of scintillator crystals 601 and substituents or gaps 602 between the scintillator crystals of the array. The scintillator crystals 601 may be spaced apart by the substituents or gaps 602. The distribution of the substituents or gaps 602 may be according to a sparsity rule.

In some embodiments, the scintillator 701 may be directly coupled to the photodetector 702. For instance, the output end of the scintillator 701 may be directly coupled to the input end of the photodetector 702. In some embodiments, the scintillator 701 and the photodetector 702 may be indirectly coupled via a light transmitting intermediate including, for example, an optical fiber, an optical fiber bundle, an optical glue, an optically coupling material, an immersion oil, or the like, or a combination thereof.

Figure 8B:
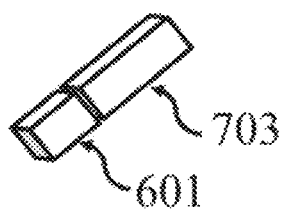

FIG. 8B illustrates a one-to-one coupling between a scintillator crystal 601 and a photodetector element 703 according to some embodiments of the present disclosure. As used herein, a one-to-one coupling between a scintillator crystal and a photodetector element may indicate that the optical signal detected in a scintillator crystal may be transmitted to a photodetector element. In some embodiments, the output end of a scintillator crystal 601 may be directly coupled to the input end of a photodetector element 703. In some embodiments, the output end of a scintillator crystal 601 of the scintillator 701 may be indirectly coupled to the input end of a photodetector element 703 of the photodetector 702 via, for example, a light transmitting intermediate.

Figure 8C:
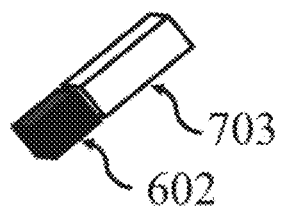

FIG. 8C illustrates the one-to-one coupling between a substituent and a photodetector element according to some embodiments of the present disclosure. In some embodiments, one end of a substituent 602 may be directly coupled to the input end of a photodetector element 703. In some embodiments, one end of the substituent 602 may be indirectly coupled to the input end of the photodetector element 703 via a light transmitting intermediate.

Various embodiments of the present disclosure may include other ways of coupling between the scintillator of a sparse detector and the photodetector. For example, in some embodiments, the photodetector may have a sparse configuration as well. The photodetector may include substituents or gaps among the photodetector elements, and the photodetector elements may be spaced apart by the substituents or gaps. In some embodiments, the photodetector elements may be spaced apart according to a sparsity rule. In some embodiments, the photodetector elements and the scintillator may share a same pattern. In such embodiments, one scintillator crystal of the scintillator may be coupled to one photodetector element of the photodetector.

In some embodiments where the photodetector may be a sparse photodetector, the substituents or gaps of the scintillator may be coupled to the substituents or gaps of the photodetector. Various embodiments according to the present disclosure may be ascertained to one skilled in the art. For example, the sparse photodetector may include gaps only, and the substituents or gaps in the scintillator may sit on the gaps of the sparse photodetector and uncoupled to photodetector elements. The coupling between the scintillator and the photodetector that may be used in connection with the present system described herein are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

The sparse detector according to some embodiments of the present disclosure may have several advantages. In some embodiments, compared to imaging devices with non-sparse detectors, the manufacture cost of the imaging devices with a sparse detector of the same field of view may be reduced. As mentioned above, the scintillators used in a medical imaging technology may be manufactured with a material containing a rare earth element such as, for example, Lanthanum, Lutetium, Yttrium, etc. Scintillators containing rare earth elements may be expensive due to factors including, for example, the difficulty of crystallization, the scarcity of economically exploitable ore deposits, etc. To achieve the same field of view, the imaging devices with sparse detectors may reduce the amount of the material(s) for scintillators compared to the imaging devices with non-sparse detectors. The imaging devices with sparse detectors may keep high image quality and spatial resolution during the same scanning time. The details regarding the image quality and spatial resolution will be further illustrated hereinafter.

In some embodiments, for the same amount of scintillator material, compared to non-sparse detectors, more sparse detectors may be made than non-sparse detectors. Accordingly, using the same amount of scintillator material, an imaging device with one or more sparse detectors may allow a larger or longer scan area; therefore, to scan a same area, an imaging device with one or more sparse detectors may take less time than an imaging device without a sparse detector.

In some embodiments, when a same area is scanned, compared to an imaging devices with non-sparse detectors, an imaging device with sparse detectors may acquire less data (due to the absence of one or more scintillator crystals), and thereby reducing the consumption of the bandwidth or channels of the processing electronics. A sparse detector may receive fewer projections than a non-sparse detector. The total volume of data to be processed may be reduced. Thus, the need for the bandwidth or channels of the processing electronics may be reduced.

Figure 9:
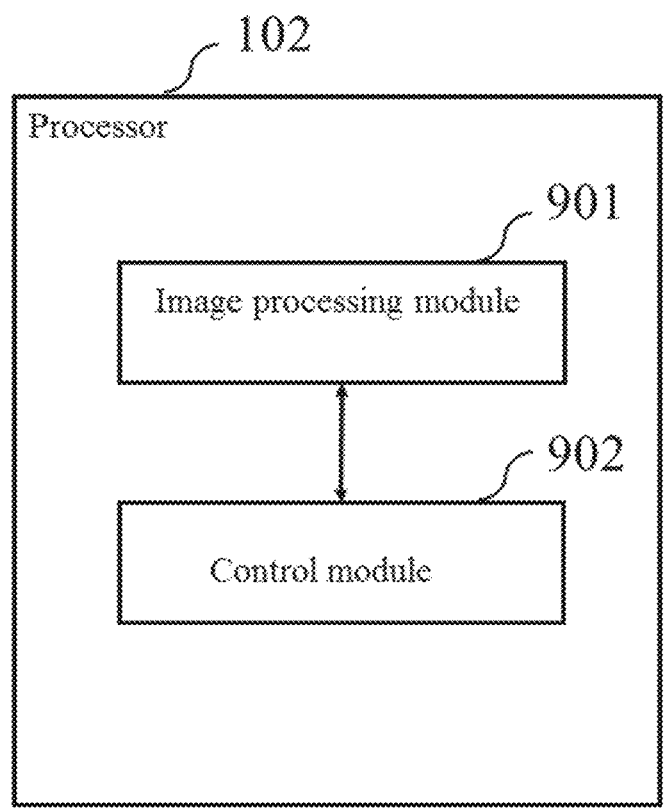
FIG. 9 is a block diagram illustrating the configuration of a processor of an imaging system according to some embodiments of the present disclosure.

FIG. 9 is a block diagram illustrating a processor 102 of an imaging system according to some embodiments of the present disclosure. It should be noted that a processor described below is merely provided for illustrating an example of the processor, and not intended to limit the spirit and scope of the present disclosure. The processor 102 may be configured to process the signals or instructions received from the image devices 101, the terminal 103, the database 104, or other modules or units in the system and it may send information to the modules or units in the system. For example, it may perform functions of image processing and controlling the operation of the imaging device 101. It should be noted that the above description about the structure of the processor 102 is merely an example, and is not intended to be limiting. In some embodiments, the processor 102 may include other modules, and the modules may be integrated into one module to function together as needed.

Referring to FIG. 9, the processor 102 may include an image processing module 901 and a control module 902. The image processing module 901 may be configured to perform the functions including image reconstruction, image correction and preprocessing. The image processing module 901 may receive the signals or instructions from or send information to the image devices 101, the terminal 103, the database 104, the control module 902, or other modules or units in the system. More details about the functions and structures of the image processing module 901 will be described in FIG. 10.

The control module 902 may be configured to control different components of the imaging system in order to achieve optimal analysis of the target, and it may receive signals or instructions from or send information to the image devices 101, the terminal 103, the database 104, the image processing module 901, or other modules or units in the system. In some embodiments, the control module 902 may control the image devices, for example, it may control the position of the detector modules 301, the position of the target, the rotation speed of the gantry in the system. In some embodiments, the control module 902 may control the data storage of the imaging system, including the storage location of data, the content of the data, the way to store, or the like, or any combination thereof. For example, the control module 902 may determinate when and/or in which format the imaging data are stored in the database 104, and/or determinate whether to store the imaging data or the output data of the image processing module 901 in the database 104. In some embodiments, the control module 902 may control the image processing module 901. For example, it may control the image processing module 901 to select different reconstruction algorithms and/or correction algorithms to process the imaging data. In some embodiments, the control module 902 may control the terminal 103. For example, the control module 902 may transmit some commands to terminal 103, including the size of an image, the location of an image, or the length of time an image remaining on a display screen. In some embodiments of the present disclosure, the image may be divided into several sub-portions for display, and the control module 902 may control the number of the sub-portions.

It should be noted that the above description about the control module 902 is merely an example, and not intended to limit the scope of the present disclosure. For persons having ordinary skills in the art, multiple variations and modifications may be made under the teachings of the present disclosure. For example, the control module 902 may also control data transmission of the imaging system. In some embodiments, the control module 902 may determinate when, how, and/or whether, the imaging data obtained from the imaging device 102 should be transmitted to the image processing module 901. In some embodiments, the control module 902 may determinate whether the output information from the imaging device 101, the processor 102, the terminal 103, and the database 104 should be transmitted in the network 105. In some embodiments, the control module 902 may determinate when, how, and/or whether, the terminal 103 may receive input, or present output information.

Although certain embodiments have been described above, these embodiments have been presented by way of example only. It is obvious that to those skilled in the art, after understanding the basic principles of the processor 102, the modules of the processor 102 may be modified or varied without departing from the principles. The modifications and variations are still within the scope of the present disclosure.

Figure 10:
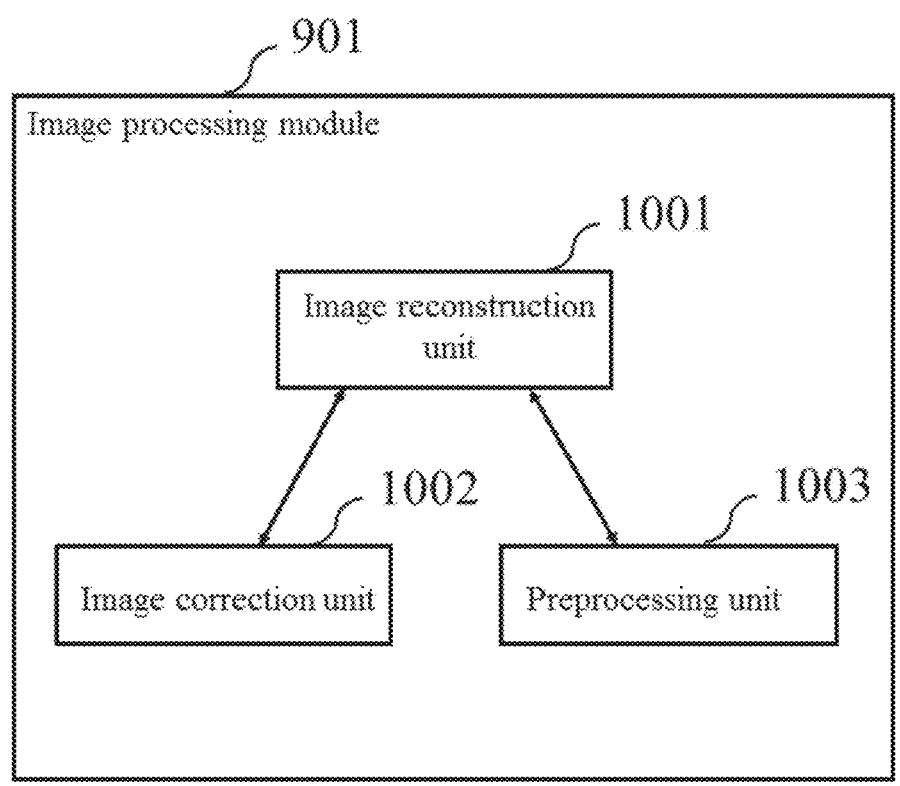
FIG. 10 is a block diagram illustrating an image processing module of a processor according to some embodiments of the present disclosure.

FIG. 10 is a block diagram illustrating an image processing module 901 of the processor 102 according to some embodiments of the present disclosure. As illustrated in FIG. 10, the image processing module 901 may include an image reconstruction unit 1001, an image correction unit 1002, and a preprocessing unit 1003. It should be noted that the above description about the structure of the image processing module 901 is merely an example, and is not intended to be limiting. In some embodiments, the image processing module 901 may include other units, and the units may be integrated into one unit to function together as needed.

Referring to FIG. 10, in some embodiments, the image reconstruction unit 1001 may use a reconstruction algorithm to reconstruct the imaging data received. The reconstruction algorithm may be an analytic reconstruction algorithm, an iterative reconstruction algorithm, or based on compressed sensing (CS). Analytic reconstruction algorithms may be a filtered backprojection (FBP) algorithm, a back projection filtration (BPF) algorithm, a ρ-filtered layergram, or the like. Iterative reconstruction algorithms may be an ordered subset expectation maximization (OSEM) algorithm, a maximum likelihood expectation maximization (MLEM) algorithm, or the like. In some embodiments, the algorithm mentioned above may be combined with some support constraints. The support constraints may be predefined according to some factors such as the arrangement of scintillator crystals on a detector, or the arrangement of the detectors in the imaging devices, or other parameters such as, image resolution, sensitivity, stability, the size of the crystals, or the like, or any combination thereof. It should be noted that any reconstruction technique based on mathematic and statistical knowledge of the data acquisition process, and geometry of the imaging system disclosed herein, is acceptable to be used in the image reconstruction unit 1001.

The image correction unit 1002 may be configured to modify the imaging data generated from the imaging device 101, the image generated from the image reconstruction unit 1001, or the like, or any combination thereof. For instance, the image correction unit 1002 may modify low-quality images resulting from, for example, calibration problems, detector failure, resolution and partial volume effects, patient motion, attenuation, scatter, or other factors that may influence the image quality, or a combination thereof. In some embodiments, the image correction unit 1002 may perform its function before, after, or in combination with the process of the image reconstruction. For example, when an iterative reconstruction algorithm is used in the process of the image reconstruction, after each of iteration, the image correction unit 1002 may perform correction. As another example, the image correction unit may perform correction due to a physical characteristic of the imaging device including, for example, scatter, random coincidences, attenuation, normalization, etc., before image reconstruction, while perform decay correction after the image is reconstructed. It should be noted that the above description about the image correction unit 1002 is merely an example according to the present disclosure. Obviously, to those skilled in the art, after understanding the basic principles of the image correction unit, the form and details of the process may be modified or varied without departing from the principles. The modifications and variations are still within the scope of the current disclosure described above.

Still referring to FIG. 10, in some embodiments, the preprocessing unit 1003 may be configured to process the information used to reconstruct and/or correct the image, or the like, or any combination thereof. For example, the preprocessing unit 1003 may determinate whether the output data from any step of image reconstruction and image correction meet a predefined threshold. Merely by way of example, the predefined threshold may be a desired image resolution, the total number of iterations in iterative image reconstruction, clinically acceptable view of the target, and/or the acceptable degree of variation of the reconstructed images, etc. In some embodiments, the preprocessing unit 1003 may perform its function before, after, or in combination with the image processing step and/or the image correction step.

While certain embodiments have been described above, these embodiments have been presented by way of example only, and are not intended to limit the scope of the present disclosure. Furthermore, various omissions, substitutions, and changes in the form of the methods and systems described herein may be made without departing from the spirit and the scope of the inventions.

Figure 11:
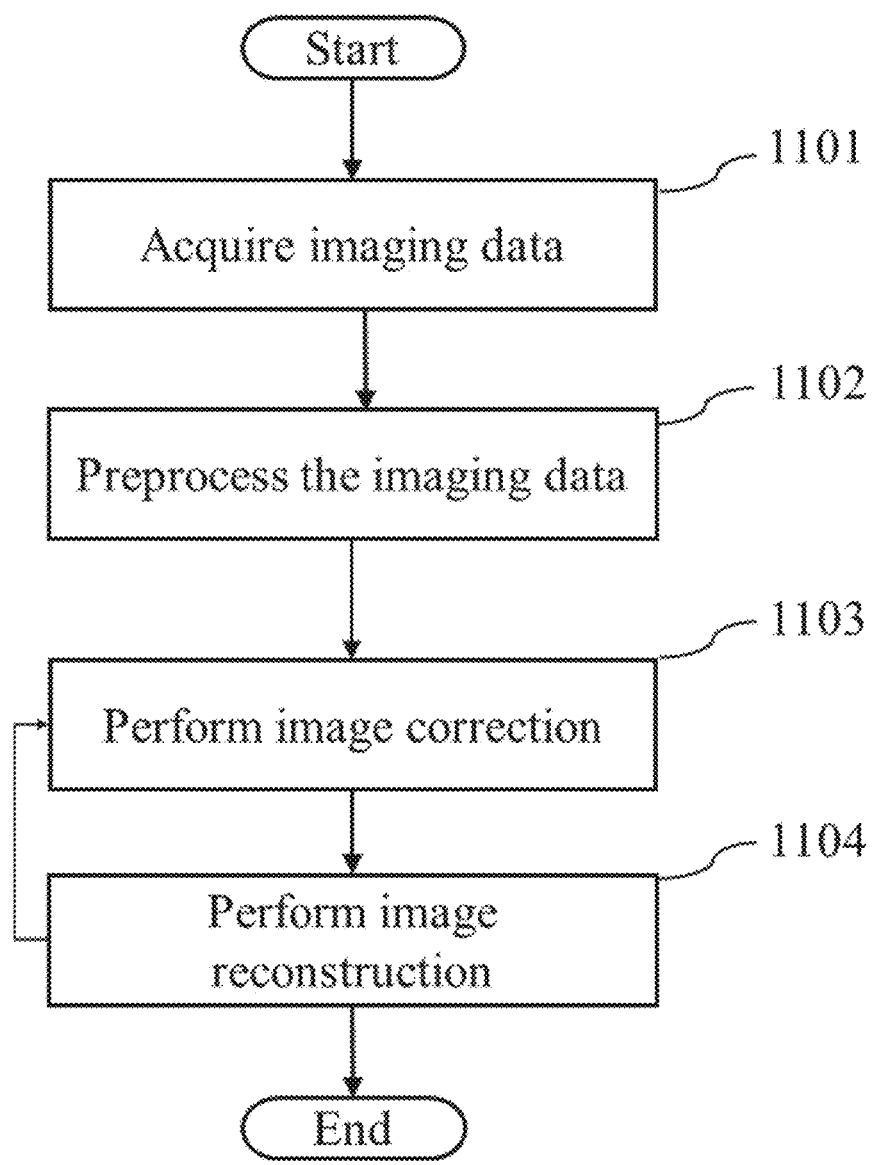
FIG. 11 is a flowchart illustrating a process of image processing according to some embodiments of the present disclosure.

FIG. 11 is a flowchart illustrating a process of image processing according to some embodiments of the present disclosure. It should be noted that the steps described here is merely an example, and is not intended to be limiting.

In step 1101, imaging data may be acquired. The acquisition may be accomplished by the processor 102, or other modules or units capable of acquiring data in the system. In some embodiments, the imaging data may be acquired from the imaging device where a target may be under examination. The imaging data acquired may be stored in the database 104 or other modules or units capable of storing data. The storage format of imaging data acquired may include, without limitation, listmode or sinogram.

In step 1102, the acquired imaging data may be preprocessed. The imaging data acquired may be preprocessed by the preprocessing unit 1003 of the image processing module 901 of the processor 102, or other modules or units capable of processing data in the system. The imaging data preprocessing may be performed in parallel to, or, as needed, after all imaging data has been acquired. The imaging data acquired may be preprocessed in a listmode format or in a sinogram format, and the sinogram format may be converted from the listmode format. In some embodiments, the preprocessing of the acquired imaging data may include, without limitation, generating virtual scintillator units based on actual scintillator crystals, calculating the efficiency of virtual scintillator units and the line of response, estimating spatial resolution, etc. The preprocessed imaging data may be stored in the database 104. The storage format of preprocessed imaging data may include, without limitation, listmode or sinogram. The storage method may include, without limitation, sequential storage, linked storage, indexed storage, hashing storage, or the like, or a combination thereof.

In step 1103, image correction may be performed. The image correction may be accomplished by the image correction unit 1001 of the image processing module 901 of the processor 102. Image correction may include, without limitation, correction for random coincidences, estimation and subtraction of scattered photons, detector dead-time correction (after the detection of a photon, the detector may need to "cool down"), correction for radioactive nuclide decay, detector-sensitivity correction (for both inherent detector sensitivity and changes in sensitivity due to an angle of incidence), correction for attenuation due to absorption of coincidence events in the target or scattering out of the detector field of view, or the like, or a combination thereof. The corrected images may be stored in the database 104. The storage method may include, without limitation, sequential storage, linked storage, indexed storage, hashing storage, or the like, or a combination thereof.

In step 1104, the corrected imaging data may be reconstructed by using a reconstruction algorithm. The reconstruction of preprocessed imaging data may be accomplished by the image reconstruction unit 1001 of the image processing module 901 of the processor 102. The algorithm used to reconstruct images may include, without limitation, filtered back-projection (FBP), maximum likelihood Expectation maximum (MLEM), ordered subset expectation maximum (OSEM), or Complete Ordered Subset Expectation Maximum (C-OSEM), or an algorithm based on compressed sensing (CS). In some embodiments, the reconstruction method may include treating each detector as a separate entity, so that only coincidences within a detector are detected. The imaging data from each detector may then be reconstructed individually (2D reconstruction). In some embodiments, the reconstruction method may include allowing coincidences to be detected between detectors as well as within detectors, then reconstructing the entire volume together (3D reconstruction). Three-dimensional reconstruction techniques have better sensitivity (because more coincidences may be detected and used) and therefore less noise than two-dimensional reconstruction techniques. Three-dimensional reconstruction techniques may be sensitive to the effects of scatter and random coincidences, and may consume greater computer resources, compared to two-dimensional reconstruction techniques. The reconstruction of preprocessed imaging data may be performed in parallel to, or after all imaging data has been preprocessed, as needed. The reconstruction may be conducted based on sinogram converted from part of or all listmode preprocessed imaging data, or based on listmode preprocessed imaging data directly. Reconstructed imaging data may be stored in the database 104. The storage method may include, without limitation, sequential storage, linked storage, indexed storage, hashing storage, or the like, or a combination thereof. Reconstructed images may include a two-dimensional (2D) image, a three-dimensional (3D) volume, a 3D volume over time (4D), etc. The system may output reconstructed images. The reconstructed images may be provided for display, to a printer, a computer network, or one or more other devices.

In some embodiments, the reconstructed image may be corrected using image correction algorithms. For example, decay correction may be performed to compute the decay rate of the number or particles at a later time point relative to when they were measured. In some embodiments, the corrected image may be reconstructed again. In some embodiments, the corrected image may be stored and output.

It should be noted that the above description about the process of processing imaging data and obtaining an image is merely an example according to the present disclosure. Obviously, to those skilled in the art, after understanding the basic principles of the process of processing imaging data and obtaining an image, the form and details of the process may be modified or varied without departing from the principles.

Figure 12:
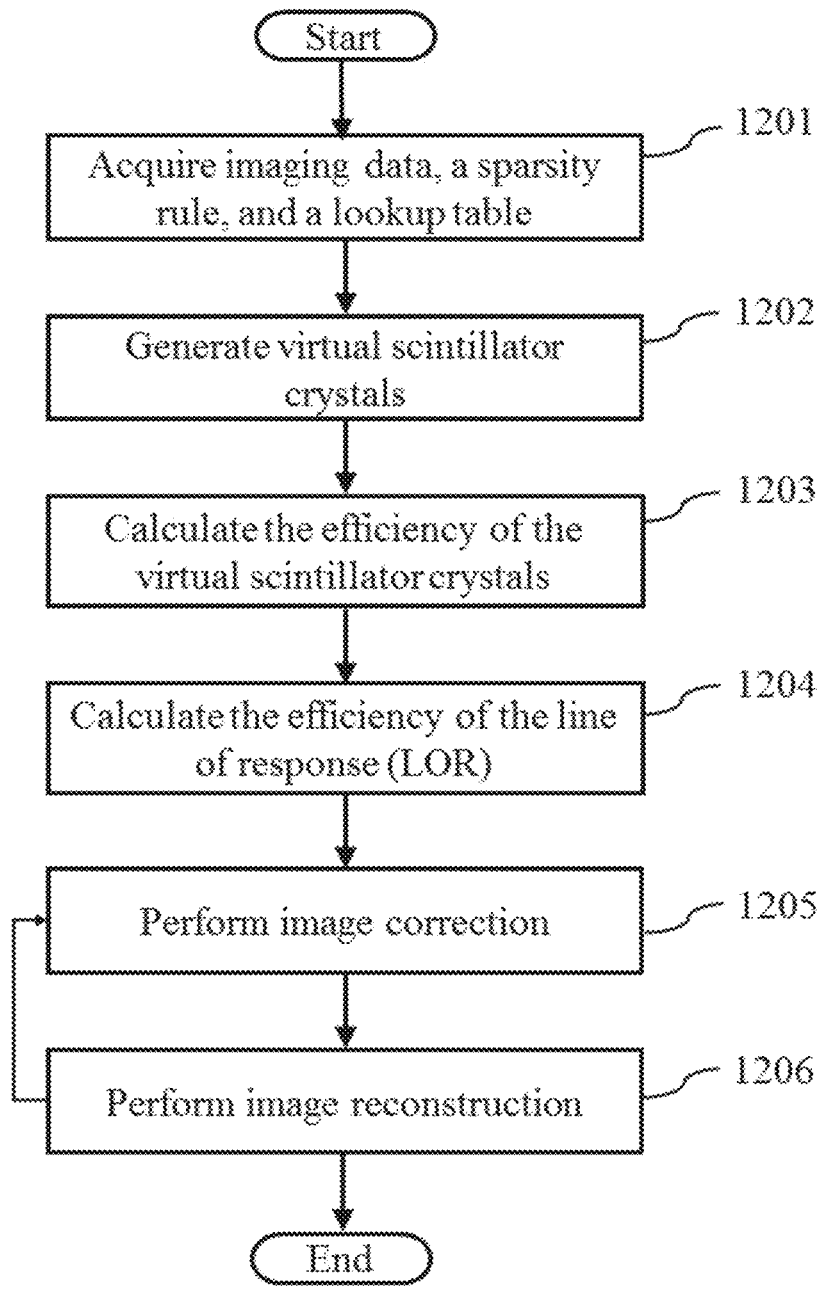
FIG. 12 is a flowchart illustrating another process of image processing according to some embodiments of the present disclosure.

FIG. 12 illustrates a process for processing imaging data and obtaining an image according to some embodiments of the present disclosure. It should be noted that the steps described here is merely an example, and is not intended to be limiting.

In step 1201, imaging data may be acquired. Based on the configuration of the scintillator crystals of the detectors according to a sparsity rule, a lookup table of the scintillator crystals may be obtained. This step may be performed by the image processing module 901 of the processor 102 in the system. It should be noted that, the imaging data may be obtained before, after, or around the same time that the lookup table of the scintillator crystals is obtained. In some embodiments, the scintillator crystals of the detectors may be arranged in a uniform pattern, for example, a checkerboard pattern, a stepped pattern. In some embodiments, the scintillator crystals of the detectors may be arranged by being spaced along the circumferential direction or along the axial direction, or the both. The space in the row may be the same with of different from that in the column. In some embodiments, the scintillator crystals of the detectors may be arranged according to a sparsity rule. For instance, according to a sparsity rule, at most one scintillator crystal may be removed out of every two scintillator crystals in a plurality of scintillator crystals. See relevant description elsewhere in the present disclosure. In some embodiments, the scintillator crystals of the detectors may be arranged randomly with a sparsity predefined according to considerations including, for example, image resolution, sensitivity, stability, the size of the crystals, or the like, or any combination thereof. The sparsity may be any value between 0 and 1. The lookup table obtained in the step may be a two-dimensional map that may be referred as a position map of scintillator crystals in a detector. In some embodiments, if one position is occupied by a scintillator crystal, the corresponding location in the lookup table may be denoted as 1; while if the position is not occupied by a scintillator crystal, the corresponding location in the lookup table may be denoted as 0.

According to the lookup table generated in step 1201, virtual scintillator units may be generated in step 1202, and the step may be performed by the preprocessing unit 1003 of the image processing module 901 of the system. In some embodiments, the term "virtual scintillator unit" may refer to a unit including what exists in two or more positions (for example, neighboring positions) along one direction, for example, along the axial direction of the gantry within which the detector is placed. A position may refer to where a scintillator crystal may be positioned. In a sparse detector, a position may be occupied by a scintillator crystal, or may be void (or referred to as gap) or occupied by a substituent.

Merely by way of example, a virtual scintillator unit may include what exists in two neighboring positions along the axial direction of the gantry within which the detector is placed. In some embodiments, the virtual scintillator unit may include two scintillator crystals when each of the two positions is occupied by a scintillator crystal. In some embodiments, the virtual scintillator unit may include one scintillator crystal when one of the two positions is occupied by a scintillator crystal and the other position is a void (or gap) or occupied by a substituent. In some embodiments, the virtual scintillator unit may include no scintillator crystal when each of the two positions is a void or occupied by a substituent.

A virtual scintillator unit may include an arbitrary number of scintillator crystals, e.g., zero, one, two, three, four. In some embodiments, a virtual scintillator unit in a detector may include the same number scintillator crystals. In some embodiments, at least two virtual scintillator units in a detector may include different numbers of scintillator crystals.

In some embodiments, the imaging data acquired in step 1201 may be stored in the listmode, in some embodiments, the imaging data acquired in step 1201 may be stored in sinogram.

In some embodiments, a virtual scintillator unit may be generated by the expression below:

$$Crystal_N(ia,Ra)=Crystal(ia,2Ra)+Crystal(ia,2Ra+1), \quad Ra=0,1,2\ldots, \tag{1}$$

where (ia, Ra) may be denoted as a location on a detector wherein ia may represent the number in the circumference direction, Ra may represent the number in the axial direction, $Crystal_N$ may represent the virtual scintillator units, and Crystal(ia, 2Ra) may indicate whether the location (ia, 2Ra) may be occupied by a scintillator crystal.

In step 1203, the efficiency of the virtual scintillator units may be calculated. The step may be performed by the preprocessing unit 1003 of the image processing module 901 of the system. The efficiency of the virtual scintillator units as used herein may refer to the number of scintillator crystals in a virtual scintillator unit. In some embodiments, the efficiency of the virtual scintillator units may be calculated according to the lookup table established in step 1201, for example, $$Ca(ia,Ra)=0.5*(Lut(ia,2Ra)+Lut(ia,2Ra+1)), \tag{2}$$

where Ca may represent the efficiency of the virtual scintillator unit, Lut may represent the value in the lookup table. In some embodiments, if one position is occupied by a scintillator crystal, the corresponding location in the lookup table may be denoted as 1, while if the position is not occupied by a scintillator crystal, the corresponding location in the lookup table may be denoted as 0. It should be noted that the expression described above is merely an example, and is not intended to limiting. In some embodiments, the expression above may be varied, for example, the number of the term used to be added together may be larger than two, the term may be in a same circumference direction, or be in different rows or in different columns, or the coefficient front may be varied in some circumstance.

After the efficiency of the virtual scintillator units was generated, the efficiency of the line of response (LOR) of a coincidence event may be calculated in step 1204. The step may be performed by the preprocessing unit 1003 of the image processing module 901 of the system. The efficiency of the line of response used as herein may refer to the product of the efficiency of virtual scintillators. In some embodiments, the efficiency of the line of response may be calculated according to the expression below:

$$C_{lor}=1/(Ca*Cb), \tag{3}$$

where $C_{lor}$ may represent the efficiency of the line of response, and Ca and Cb may represent the efficiencies of the virtual scintillator units on which two photons of a coincidence event in the same line of response (LOR) may incident respectively. It should be noted that the expression described above is merely an example, and is not intended to limiting. In some embodiments, the expression may be varied in some circumstance.

In step 1205, image correction may be performed, and the step may be performed by the image correction unit 1002 of the image processing module 901 or other modules or units capable of correcting image in the system. The image correction may include attenuation correction, scatter correction, one or more other corrections that may influence the image quality, or a combination thereof. Various methods for attenuation correction and scatter correction that are known in the art may be used in connection with the present system. In some embodiments, a map showing attenuation properties of the target and/or its surrounding environment may be constructed and projected to correct photon attenuation in the reconstructed image, for example, a PET image. In some embodiments, an attenuation map may be constructed based on imaging information generated by a different imaging modality of the multi-modality imaging system, such as MRI and/or CT.

Then, in step 1206, image reconstruction may be performed, and the step may be performed by the image reconstruction unit 1001 of the image processing module 901 or other modules or units capable of reconstructing image in the system. The reconstruction algorithm used in the step may be an analytic reconstruction algorithm, an iterative reconstruction algorithms, or based on compressed sensing (CS). Analytic reconstruction algorithms may be a filtered backprojection (FBP) algorithm, a back projection filtration (BPF) algorithm, a ρ-filtered layergram, or the like. Iterative reconstruction algorithms may be an ordered subset expectation maximization (OSEM) algorithm, a maximum likelihood expectation maximization (MLEM) algorithm, or the like. In some embodiments, the algorithm mentioned above may be combined with some support constraints. The support constraints may be predefined according to some factors such as the arrangement of scintillator crystals on a detector, or the arrangement of the detectors in the imaging devices, or other parameters such as, image resolution, sensitivity, stability, the size of the crystals, or the like, or any combination thereof.

For illustration purposes, the OSEM method may be described below. In this method, a pre-specified starting image may be needed, and the imaging data may be divided into several subsets, and the number of subsets may be set based on parameters including, for example, the time of image reconstruction (e.g., the time available for image construction), image quality, the size of detector, the amount of imaging data, or the like, or a combination thereof. The iterative process may be described as the expression below:

$$f_j^{(n+1)} = \frac{f_j^{(n)}}{\sum_{i_k \in s_k} M_{i_k j}} \sum_{k \in S} M_{i_k j} \left( \frac{c_{lor}}{\sum_{j_p \in L_k} M_{i_k j_p} f_{j_p}^{(n)}} \right), \quad (4)$$

where $f_j^{(n)}$ may represent the imaging data of the jth pixel in the nth iteration, $S_k$ may represent k th subset, $L_{i_k}$ may represent the $i_k$ th LOR in k th subset, $f_{j_p}^{(n)}$ may represent the imaging data of the $j_p$ th pixel of the $L_{i_k}$ th LOR, M may represent the system matrix, and $C_{lor}$ may represent the efficiency of the line of response. After several times of iteration, the data of the image that may meet the demands of the image quality may be obtained.

It should be noted that the above description about the process of processing imaging data and obtaining an image is merely an example according to the present disclosure. Obviously, to those skilled in the art, after understanding the basic principles of the process of processing imaging data and obtaining an image, the form and details of the process may be modified or varied without departing from the principles. In some embodiments, other steps may added in the process, for example, the intermediated data and/or the final data of the process may be stored in the process, and the storage location may be in database 104 or other modules or units capable of storing data. In some embodiments, the order of the steps may be varied. For example, the steps 1202, 1203, 1204 and the process of establishing a lookup table may be performed before the imaging data is acquired, and the system may be corrected before scanning a target. The modifications and variations are still within the scope of the current disclosure described above.

Figure 13:
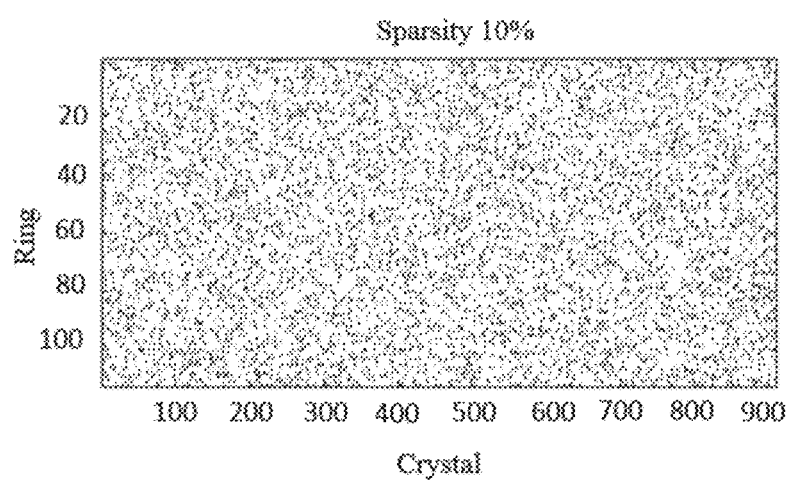
FIG. 13 illustrates an exemplary configuration of scintillator crystals in a sparse detector according to some embodiments of the present disclosure.

FIG. 13 illustrates an exemplary configuration of scintillator crystals in a sparse detector according to some embodiments of the present disclosure. In such embodiments, a plurality of sparse detectors may form a detector ring. Multiple detector rings may arrange along the axial direction of a gantry. Referring to the figure, the horizontal axis may represent the number of scintillator crystals along the circumferential direction of the gantry, and the vertical axis may represent the number of scintillator crystals in detector rings along the axial direction. Black dots in FIG. 13 may represent substituents or gaps, and blank area may represent scintillator crystals. As illustrated in FIG. 13, the distribution of the substituents or gaps may be according to a sparsity rule. The sparseness of the scintillator crystals in the sparse detector may be 10%. It should be noted that the configuration of scintillator crystals in a sparse detector used herein is merely an example according to the present disclosure, not intended to be limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the present disclosure are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

We claim:

1. An apparatus comprising
a sparse detector, the sparse detector comprising:
an array of scintillator crystals generating scintillation in response to radiation, at least a portion of the scintillator crystals being spaced apart according to at least one sparsity rule; and
an array of photodetector elements configured to generate an electrical signal in response to the scintillation,
wherein at least a portion of the array of photodetectors are coupled to the array of scintillator crystals, and
a processor configured to:
obtain imaging data from the sparse detector;
generate a plurality of virtual scintillator units according to the at least one sparsity rule related to the sparse detector;
calculate efficiencies of the virtual scintillator units;
calculate an efficiency of a line of response based on the efficiencies of the virtual scintillator units; and
generate, based on the efficiency of the line of response and the imaging data, an image.

2. The apparatus of claim 1, wherein at least a portion of the array of scintillator crystals are spaced apart by one or more blocks of a light-transmitting material.

3. The apparatus of claim 2, wherein the size of a block of the one or more blocks of the light-transmitting material is substantially equal to the size of a scintillator crystal of the array of scintillator crystals.

4. The apparatus of claim 2, wherein the light-transmitting material comprises glass.

5. The apparatus of claim 1 comprising a gap between two scintillator crystals of the array of scintillator crystals.

6. The apparatus of claim 5, wherein the size of the gap is substantially equal to the size of one scintillator crystal of the array of scintillator crystals.

7. The apparatus of claim 1, wherein the at least one sparsity rule comprises removing at most one scintillator crystal out of every two neighboring scintillator crystals among the array of scintillator crystals.

8. The apparatus of claim 1, wherein the shape of a sparse detector is a block, an arc, a ring, a rectangle, or a polygon.

9. The apparatus of claim 1, wherein the apparatus comprises two detector modules parallel to each other, at least one of the two detector modules comprising one or more sparse detectors.

10. The apparatus of claim 1, wherein the apparatus comprises detector modules forming a polygon, at least one of the detector modules comprising one or more sparse detectors.

11. The apparatus of claim 1, wherein the apparatus comprises sparse detectors forming a ring.

12. An imaging system comprising:
an apparatus comprising a plurality of sparse detectors that generate imaging data; and
a processor configured to:
generate a plurality of virtual scintillator units according to a sparsity rule related to at least one of the plurality of sparse detectors;
calculate efficiencies of the virtual scintillator units;
calculate an efficiency of a line of response based on the efficiencies of the virtual scintillator units; and
generate, based on the imaging data and the efficiency of the line of response, an image.

13. The imaging system of claim 12, the imaging system being a Computed Tomography (CT) system, a Digital Radiography (DR) system, a Positron Emission Tomography (PET), a Single Photon Emission Computed Tomography (SPECT) system, a Computed Tomography-Positron Emission Tomography (CT-PET) system, a Computed Tomography-Magnetic Resonance Imaging (CT-MRI) system, a Positron Emission Tomography-Magnetic Resonance Imaging (PET-MRI) system, a Single Photon Emission Computed Tomography-Positron Emission Tomography (SPECT-PET) system, an X-ray security system or an X-ray foreign matter detection system.

14. A method comprising:
acquiring imaging data using an array of scintillator crystals;
generating, by a processor, a plurality of virtual scintillator units according to a sparsity rule related to the array of scintillator crystals;
calculating, by the processor, efficiencies of the virtual scintillator units;
calculating, by the processor, an efficiency of a line of response based on the efficiencies of the virtual scintillator units; and
reconstructing, by the processor, an image based on the imaging data and the efficiency of the line of response.

15. The method of claim 14, further comprising spacing apart at least a portion of the array of scintillator crystals by one or more blocks of a light-transmitting material.

16. The method of claim 14, wherein the sparsity rule comprises removing at most one scintillator crystal out of every two neighboring scintillator crystals among the array of scintillator crystals.

17. The method of claim 14, further comprising performing image correction by the processor.

18. The method of claim 14, wherein the generating the plurality of virtual scintillator units according to the sparsity rule related to the array of scintillator crystals comprises:
generating a lookup table relating to the array of scintillator crystals; and
generating the plurality of virtual scintillator units based on the lookup table.

19. The method of claim 18, wherein the calculating efficiencies of the virtual scintillator units comprises:
   for each of the virtual scintillator units, determining an average value of a first value and a second value in the lookup table, wherein the first value and the second value correspond to two locations associated with the virtual scintillator unit.

20. The method of claim 14, wherein the calculating an efficiency of the line of response based on the efficiencies of the virtual scintillator units comprises:
   calculating a product of the efficiencies of the virtual scintillator units, wherein the virtual scintillator units comprise a first virtual scintillator unit and a second virtual scintillator unit which two photons of a coincidence event in the line of response hit respectively; and
   calculating the efficiency of the line of response based on the product.

* * * * *